(12) United States Patent
Keller

(10) Patent No.: US 8,499,673 B2
(45) Date of Patent: Aug. 6, 2013

(54) MICROSURGICAL CUTTING INSTRUMENTS

(75) Inventor: Christopher Guild Keller, El Cerrito, CA (US)

(73) Assignee: MynoSys Cellular Devices, Inc., Albany, CA (US)

( * ) Notice: Subject to any disclaimer, the term of this patent is extended or adjusted under 35 U.S.C. 154(b) by 429 days.

(21) Appl. No.: 12/187,090

(22) Filed: Aug. 6, 2008

(65) Prior Publication Data

US 2009/0177217 A1 Jul. 9, 2009

Related U.S. Application Data

(63) Continuation of application No. PCT/US2007/061701, filed on Feb. 6, 2007.

(60) Provisional application No. 60/765,803, filed on Feb. 6, 2006.

(51) Int. Cl.
*B26B 21/56* (2006.01)

(52) U.S. Cl.
USPC ............... 83/701; 30/314; 30/346.55; 30/357

(58) Field of Classification Search
USPC ............... 30/346.53–346.55, 346.58, 346.59, 30/314, 357; 427/2.28; 606/166, 167, 170; 83/701

See application file for complete search history.

(56) References Cited

U.S. PATENT DOCUMENTS

| | | | |
|---|---|---|---|
| 1,814,182 A | 7/1931 | Morgan | |
| 1,814,959 A | 7/1931 | Morgan | |
| 2,319,607 A | 5/1943 | Kevorkian et al. | |
| 2,408,790 A | 10/1946 | Mack | |
| 3,160,967 A | 12/1964 | Nichols | |
| 3,387,368 A | 6/1968 | Scheck | |
| 3,681,846 A * | 8/1972 | Gerber | 30/355 |
| 3,761,374 A | 9/1973 | Bromer et al. | |
| 3,762,243 A * | 10/1973 | Borrkfield | 205/122 |
| 3,890,109 A * | 6/1975 | Jones | 428/626 |
| 3,911,579 A | 10/1975 | Lane et al. | |
| 3,986,260 A | 10/1976 | Whiteford | |
| 4,534,827 A | 8/1985 | Henderson | |
| 4,598,206 A * | 7/1986 | Nelson | 250/495.1 |
| 4,640,169 A | 2/1987 | Fromson et al. | |

(Continued)

FOREIGN PATENT DOCUMENTS

| | | |
|---|---|---|
| WO | WO 96/39937 | 12/1996 |
| WO | WO 99/47341 | 9/1999 |

(Continued)

OTHER PUBLICATIONS

Archer et al., "Electrorotation studies of baby hamster kidney fibroblasts infected with herpes simplex virus type 1," *Biophys J*, vol. 76, pp. 2833-2842, May 1999.

(Continued)

*Primary Examiner* — Sean Michalski

(74) *Attorney, Agent, or Firm* — Levine Bagade Han LLP

(57) ABSTRACT

The present invention relates to methods and apparatus for self-sharpening micro surgical blades, knives and assemblies including those having a cutting edge that is less than 500 angstroms thick where the cutting edge is an exposed section of a thin planar layer or region that is supported on one or both sides by a material having a higher wear rate.

33 Claims, 22 Drawing Sheets

U.S. PATENT DOCUMENTS

| | | | |
|---|---|---|---|
| 4,647,300 A * | 3/1987 | Sheets | 65/105 |
| 4,896,424 A | 1/1990 | Walker | |
| 4,984,492 A * | 1/1991 | Gerber | 83/697 |
| 4,991,481 A | 2/1991 | Gerber | |
| 5,018,347 A | 5/1991 | Feilen | |
| 5,221,415 A | 6/1993 | Albrecht et al. | |
| 5,232,568 A | 8/1993 | Parent et al. | |
| 5,295,305 A * | 3/1994 | Hahn et al. | 30/50 |
| 5,312,643 A | 5/1994 | Yamamoto et al. | |
| 5,317,938 A | 6/1994 | de Juan, Jr. et al. | |
| 5,399,232 A | 3/1995 | Albrecht et al. | |
| 5,416,657 A | 5/1995 | Beck et al. | |
| 5,423,887 A * | 6/1995 | Love et al. | 623/2.14 |
| 5,437,656 A | 8/1995 | Shikani et al. | |
| 5,488,774 A * | 2/1996 | Janowski | 30/346.53 |
| 5,569,292 A | 10/1996 | Scwemberger et al. | |
| 5,571,174 A * | 11/1996 | Love et al. | 29/890.12 |
| 5,579,583 A | 12/1996 | Mehregany et al. | |
| 5,645,684 A | 7/1997 | Keller | |
| 5,651,900 A | 7/1997 | Keller et al. | |
| 5,662,705 A * | 9/1997 | Love et al. | 128/898 |
| 5,669,144 A * | 9/1997 | Hahn et al. | 30/346.54 |
| 5,728,089 A | 3/1998 | Lal et al. | |
| 5,792,137 A | 8/1998 | Carr et al. | |
| 5,795,648 A * | 8/1998 | Goel et al. | 428/336 |
| 5,842,387 A | 12/1998 | Marcus et al. | |
| 5,893,974 A | 4/1999 | Keller et al. | |
| 5,928,161 A | 7/1999 | Krulevitch et al. | |
| 5,944,717 A | 8/1999 | Lee et al. | |
| 5,948,255 A | 9/1999 | Keller et al. | |
| 5,980,518 A | 11/1999 | Carr et al. | |
| 5,994,160 A | 11/1999 | Niedermann et al. | |
| 6,015,599 A | 1/2000 | Keller et al. | |
| 6,075,683 A | 6/2000 | Harwood et al. | |
| 6,105,261 A * | 8/2000 | Ecer | 30/346.54 |
| 6,106,751 A | 8/2000 | Talbot et al. | |
| 6,125,007 A | 9/2000 | Beck et al. | |
| 6,207,294 B1 * | 3/2001 | Rutter | 428/609 |
| 6,260,280 B1 | 7/2001 | Rapisardi | |
| 6,263,581 B1 | 7/2001 | Forte | |
| 6,289,593 B1 * | 9/2001 | Decker et al. | 30/346.54 |
| 6,319,274 B1 | 11/2001 | Shadduck | |
| 6,319,474 B1 | 11/2001 | Krulevitch et al. | |
| 6,319,724 B1 | 11/2001 | Lewis et al. | |
| 6,330,750 B1 | 12/2001 | Meckel | |
| 6,375,148 B1 | 4/2002 | Talbot et al. | |
| 6,389,699 B1 * | 5/2002 | Ecer | 30/346.54 |
| 6,615,496 B1 | 9/2003 | Fleming et al. | |
| 6,706,203 B2 | 3/2004 | Barth et al. | |
| 7,059,054 B2 | 6/2006 | Pilchowski | |
| 7,060,367 B2 * | 6/2006 | Yamada et al. | 428/634 |
| 7,396,484 B2 | 7/2008 | Daskal et al. | |
| 7,587,829 B2 * | 9/2009 | King et al. | 30/346.54 |
| 7,963,042 B2 * | 6/2011 | Keller | 30/350 |
| 2002/0078576 A1 * | 6/2002 | Carr et al. | 30/357 |
| 2002/0142182 A1 | 10/2002 | Peker et al. | |
| 2003/0208911 A1 | 11/2003 | Fleming et al. | |
| 2004/0014787 A1 | 1/2004 | Anderson et al. | |
| 2004/0147870 A1 | 7/2004 | Burns et al. | |
| 2005/0132581 A1 | 6/2005 | Jessing | |
| 2005/0144789 A1 | 7/2005 | Pilchowski | |
| 2005/0210684 A1 * | 9/2005 | Newman | 30/350 |
| 2007/0056404 A1 | 3/2007 | Pricone | |
| 2007/0157475 A1 * | 7/2007 | King et al. | 30/346.54 |
| 2007/0275179 A1 | 11/2007 | Åstrand et al. | |
| 2009/0048537 A1 | 2/2009 | Lydon et al. | |
| 2009/0099534 A1 | 4/2009 | Lee et al. | |
| 2009/0131961 A1 | 5/2009 | Keller | |
| 2010/0024222 A1 | 2/2010 | Akari et al. | |
| 2010/0234864 A1 | 9/2010 | Keller | |
| 2010/0262174 A1 * | 10/2010 | Sretavan et al. | 606/170 |
| 2011/0177322 A1 * | 7/2011 | Ogrin et al. | 428/325 |

FOREIGN PATENT DOCUMENTS

| | | |
|---|---|---|
| WO | WO 2005/037070 | 4/2005 |
| WO | WO 2007/070745 | 6/2007 |
| WO | WO 2007/092852 | 8/2007 |

OTHER PUBLICATIONS

Coumans et al., "Axonal regeneration and functional recovery after complete spinal cord transection in rats by delayed treatment with transplants and neurotrophins," *J Neurosci*, vol. 21, pp. 9334-9344, Dec. 2001.

Folch et al., "Microfabrication of oxidation-sharpened silicon tips on silicon nitride cantilevers for atomic force microscopy," *Journal of Microelectromechanical Systems*, vol. 6, No. 4, pp. 303-306, Dec. 1997.

Heida et al., "Dielectrophoretic trapping of dissociated fetal cortical rat neurons," *IEEE Trans Biomed Eng*, vol. 48, No. 8, pp. 921-930, Aug. 2001.

Vangbo et.al., "Precise Mask Alignment to the Crystallographic Orientation of Silicon Wafers Using Wet Anisotropic Etching," *J. Micromech. Microeng.*, vol. 6, pp. 279-294, 1996.

* cited by examiner

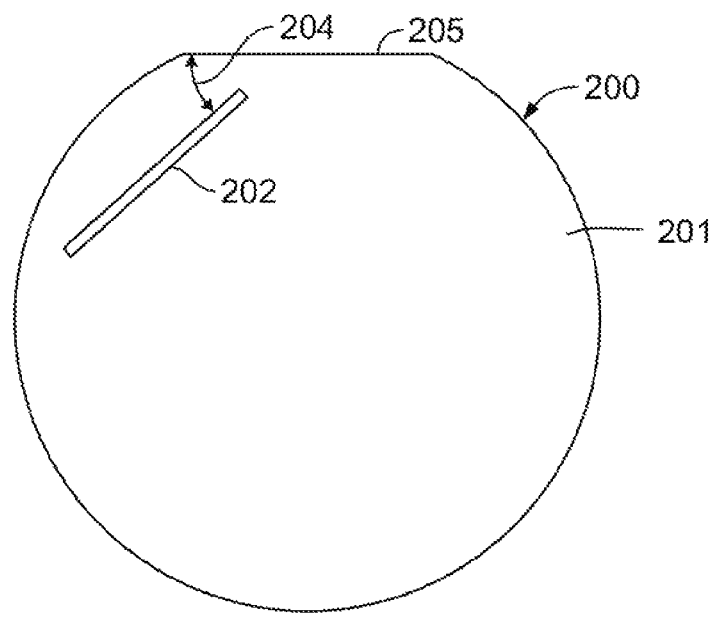
FIG. 2A
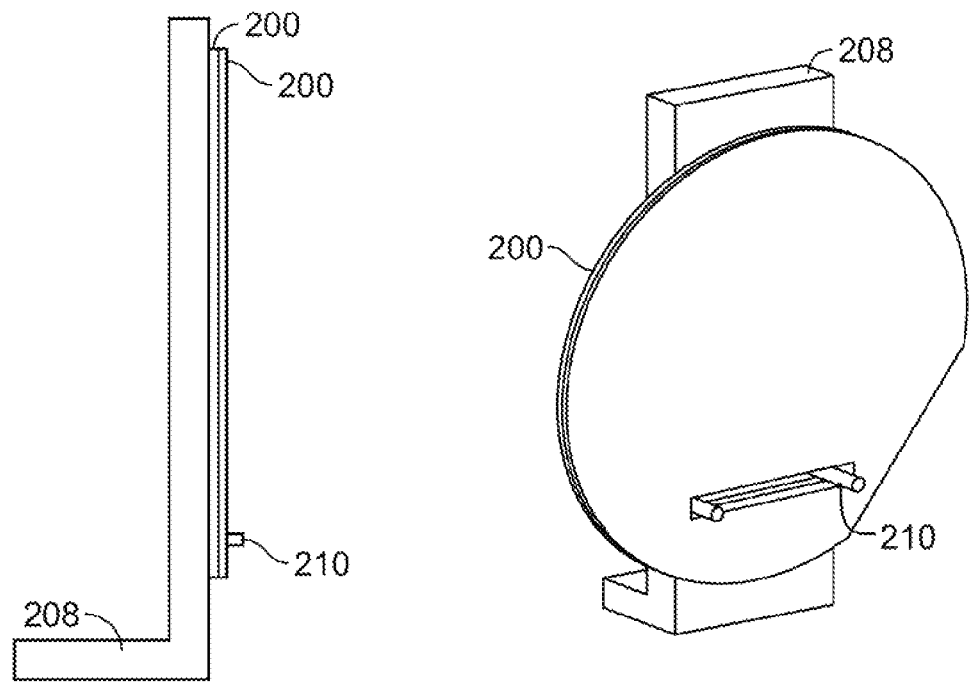
FIG. 2B
FIG. 2C

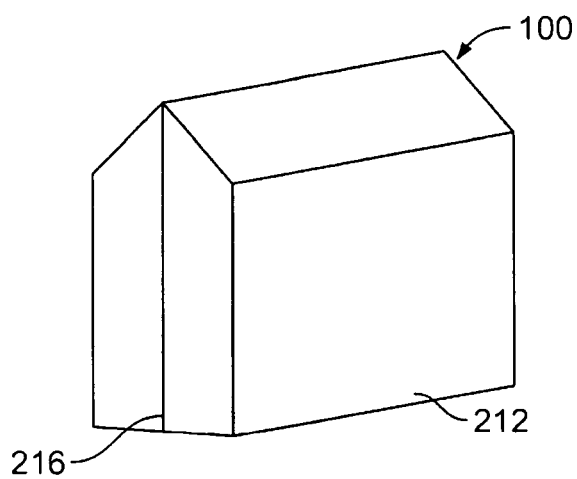
FIG. 4F
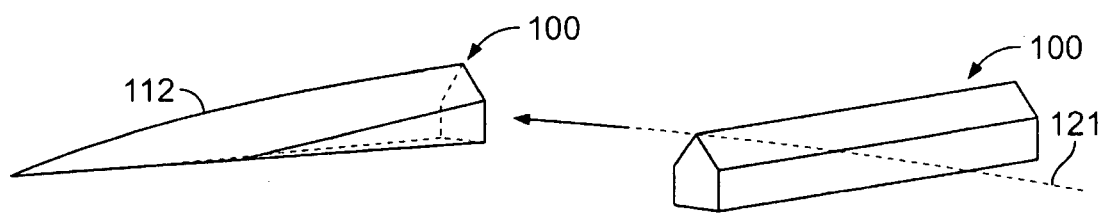
FIG. 5B  FIG. 5A

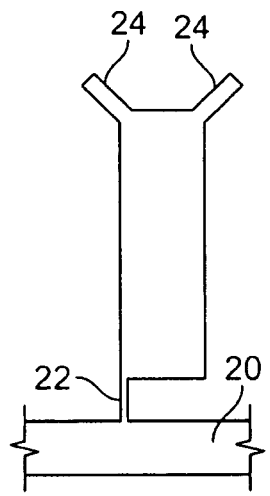
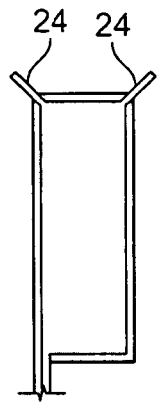
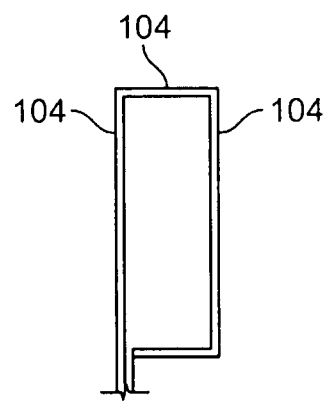
FIG. 10B     FIG. 10C     FIG. 10D
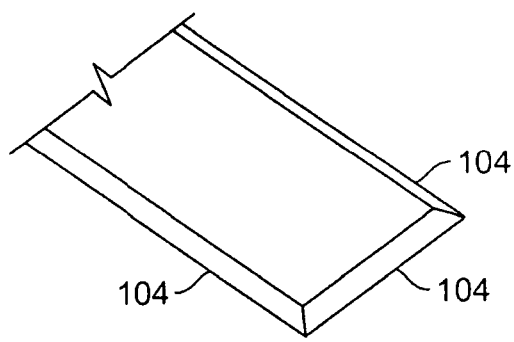
FIG. 10E
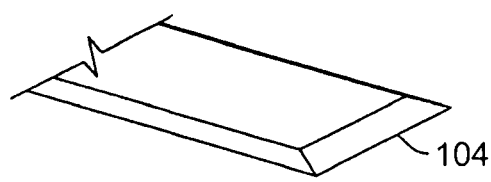
FIG. 10F
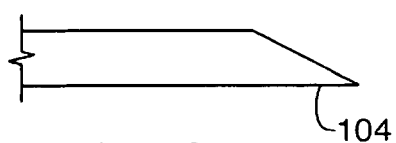
FIG. 10G

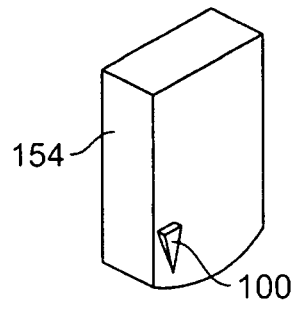 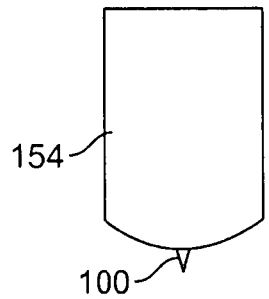 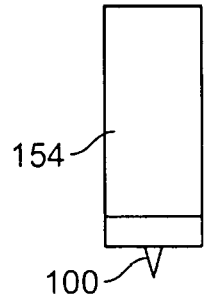
FIG. 22A  FIG. 22B  FIG. 22C
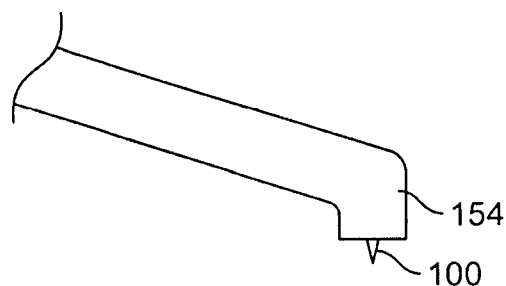
FIG. 23A
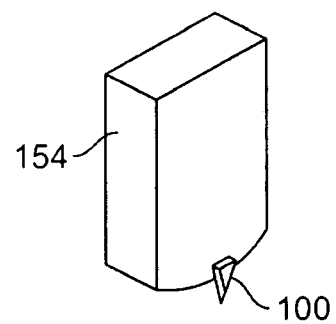 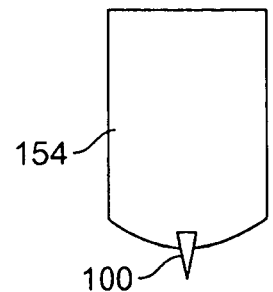 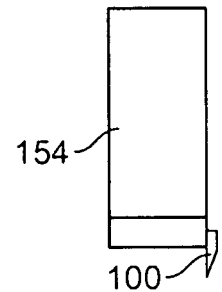
FIG. 23B  FIG. 23C  FIG. 23D

MICROSURGICAL CUTTING INSTRUMENTS

CROSS-REFERENCE TO RELATED APPLICATIONS

This application is a continuation of International PCT Application No. PCT/US2007/061701 filed Feb. 6, 2007 which claims benefit of priority to U.S. Provisional Application No. 60/765,803 filed Feb. 6, 2006, both applications of which are incorporated herewith in their entirety.

BACKGROUND OF THE INVENTION

The concept of a self-sharpening knife comes originally from observations of the incisors of rats. These teeth consist of a very hard, but very thin, front layer which is mechanically supported by a much thicker, but softer, tooth body. The sharpness of the cutting edge comes from the thinness of the hard front layer. The softer material wears away faster such that a steady state profile is maintained in normal use (gnawing) in which the tooth body slopes down away from the thin hard front cutting edge. It can never get dull because the hard layer has the same thickness down the whole length of the tooth, and it is this thickness that defines the cutting edge.

In conventional microknives made from a block of a single material (for example a diamond), the sharpness comes from the initial sharpening of the blade when it is manufactured. Even with diamond, the hardest material that exists, it is just a matter of time before atoms are worn away from the cutting edge and it becomes dull. Although diamond knives can be re-sharpened, it is difficult, requiring special skill and tools.

A self-sharpening layered knife construction (for use in large supporting structure such as the conventional sized saws and razors) is discussed in U.S. Pat. Nos. 6,105,261 and 6,389,699, the entirety of each of which is incorporated by reference. To be self-sharpening, the sharpness must come from the geometry of the construction, not the initial edge grinding. The required geometry is a thin layer of a hard material supported by a thicker layer (or layers) of softer material. The relative thinness of the hard layer is directly related to the degree of sharpness of such knives. However, the references referred to above, teach of traditional fabrication techniques and do not teach knives having a sharpness measured at the atomic level.

In fact, the use of metals to fabricate a micro-knife of atomic level dimensions is not possible because metals undergo plastic deformation at the stresses that will be encountered in cutting tissue or other materials at the atomic level. For example, a micro-knife having, dimensions 1 mm long, 0.020 mm thick, and 0.5 mm wide (and fabricated through powder metallurgy, electroplating, or diffusion bonding, etc.) is simply unsuitable for atomic level procedures. Such a knife will just be a thin piece of foil that irreversibly bends and deforms given the typical stresses encountered in such procedures.

With powder metallurgy, the starting material is a granular powder for which the size of the individual particles is greater than 1 micron. After the granular powder is compressed and heated to make a solid part, the minimum achievable layer is about 1,000 angstroms. Moreover, it is unlikely that, at the atomic level, the surface will be smooth, well defined, and of a constant thickness since it was made from relatively "lumpy" particles.

Fabrication of a blade that has a meaningful thin layer less than 500 angstroms thick requires a supporting substrate having as surface roughness less than, for example, 500 angstroms. This is not practical with a metallic substrate. Instead, substrates manufactured from ceramics, glass, and silicon are more practical to achieve angstrom-scale smooth substrates suitable for producing thin films a few angstroms thick.

In addition, the large coefficient of thermal expansion of metals greatly limits the temperature at which thin layers can be deposited without cracking upon cooling.

In view of the above, conventional metal, diamond tipped or other similar type knives have blade edges or cutting surfaces that are considerably large when viewed on an atomic scale. Typically such knives have cutting edges ranging from 500 angstroms to about 1000 angstroms. Typically, such knives provide poor surgical precision and cause unnecessary destruction of tissue when viewed at the cellular level.

Presently, atomic force microscopy uses devices having atomically sharp-tips for the manipulation and separation of cells. Such devices and methods are found in U.S. Pat. Nos. 5,221,415; 5,399,232; and 5,994,160 the entirety of each of which are incorporated by reference herein. Additional information regarding devices used in atomic force microscopy may be found in Journal of Nanoscience and Nanotechnology 2002, V 2, No. 1, pp 55-59, and Journal of Microelectromechanical Systems V 6, No. 4, December 1997, pp: 303-306 the entirety of which are also both incorporated by reference herein.

References describing the fabrication of micro knives from single crystal silicon include U.S. Pat. Nos. 5,728,089; 5,317,938; 5,579,583; 5,792,137; 5,842,387; 5,928,161; 5,944,717; 5,980,518; 6,319,474; 6,615,496; 6,706,203; and U.S. patent application nos.: 20020078576; 20030208911; 20050132581; and 20050144789 the entirety of each of which is incorporated by reference herein. Most conventional micro-knives rely on silicon as the cuttinz blade. Problems may be encountered as silicon wears too rapidly to provide a satisfactory cutting surface. As a result, silicon tends to dull quickly. Commonly assigned U.S. Provisional application No. 60/741,200 entitled: MICRO SURGICAL CUTTING INSTRUMENTS, filed on Dec. 1, 2005, the entirety of which is incorporated by reference herein, teaches improved atomic level knives and blades.

Accordingly, there remains a need for an improved atomic level microsurgical Cutting instrument that is designed to provide self-sharpening features.

SUMMARY OF THE INVENTION

The present invention is a microknife having a cutting edge that is ideally less than 100 angstroms thick, but may be less than 500 angstroms thick. This cutting edge is an exposed section of a thin planar layer or region (referred to as a cutting layer or cutting region) that is supported on one or both sides by a material (i.e., a support material) having a higher wear rate under the conditions of normal use. The term "wear rate" is defined as the rate of material removal or dimensional change due to wear, per unit of exposure parameter (e.g., per unit of distance cut, force, stress, etc.).

Variations of the invention include micro-knives having distinct layers (such as a cutting layer and a support layer) where the cutting edge is no greater than a thickness of the cutting layer. In such variations the thickness of the cutting layer required for atomic level cutting may be achieved by the fabrication techniques described herein.

Variations of the invention also include knives, including micro-knives, that do not have distinct layers but rather regions (such as a cutting region, a support region, and a transition region) where the wear rate or other characteristics transition over the transition region. These are known as "functionally gradient materials". In this case the function is wear rate, which is increasing with increasing distance from the plane of the Cutting layer. It is further contemplated that additional variations of the invention include knives that have both distinct layers as well as such regions.

Although the knives of the present invention allow for self-sharpening of the blade edge through use, the blade edge may also be sharpened via a sharpening process. For example, the supporting material may be selectively removable by a chemical process such as etching that does not affect the Cutting region/layer or removes the cutting region/layer at a reduced rate when compared to the supporting material.

In variations of the invention, the thin plane of the cutting material may be supported on only one side by the faster wearing support material and/or transition material. Normally it is preferred to have a support layer on both sides of the cutting region/layer, so that at least an atom of the cutting layer film is protected until the wear process brings it to the cutting edge. This protection allows the design to be closer to the desired limit of a layer of single atom thickness. In theory, the limit would be a cutting layer or region one atomic layer thick. However, typically the minimum thickness will be determined by the number of atoms needed to establish the material properties (e.g., hardness) of the material.

The microknives described herein can be mounted on handles for use as hand held instruments, attached to catheters, and/or attached to micromanipulators. The knives are suitable for manual operation or robotic control. The cost of the manufacturing process is also sufficiently low that the knives can be intended as disposable consumables for surgical applications. Even for one-time use, the self-sharpening aspect of the microknives is valuable since, at the atomic level, wear begins immediately with use. Conventional microknives lose their sharpness during their first use.

BRIEF DESCRIPTION OF THE DRAWINGS

FIGS. 2A-2C illustrate a variation of a process of fabricating a knife blade according to the present invention.

FIG. 4F illustrates an example of a variation of an individual knife blade.

FIG. 5A-5B illustrates one possible example of forming a knife blade into a shape for attachment to a handle or other fixture.

FIGS. 10B-10G shows how compensation patterns protect the corners of the blades during etching.

FIGS. 22A-22C shows a knife imbedded in a block with a predetermined length of the knife blade protruding from the block so that the depth of cutting is constants.

FIGS. 23A-23D show additional variations of mounting, a microknife to a block or handle.

DETAILED DESCRIPTION OF THE INVENTION

Figure 1A:
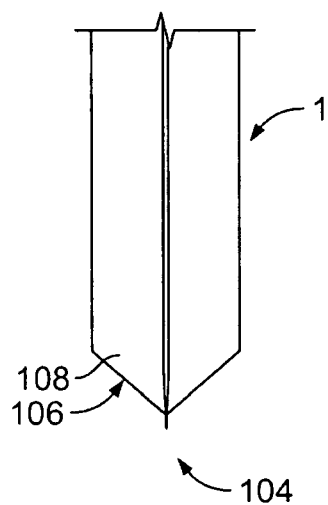
FIG. 1A shows a cross section through a variation of the blade having a double sided support.

FIG. 1A shows a cross sectional view of one variation of a microsurgical blade 100. The thin layer, or region of cutting, region 104 is supported on both sides by a thicker layer of a support material 106. As noted above, the cutting material 104 is a region in the knife that has a relatively low wear rate as compared to the supporting material 106. In one variation, the cutting region 104 is a discrete layer that is separate (clearly distinct) from any adjacent layer. In additional variations, the region 104 may transition to a support region 106 (having a higher wear rate). In the latter case, a transition region 110 will be located at the interface between Cutting and support regions. In another variation, mechanical support for the cutting layer may be entirely provided by a transition region, without another "support material."

Figure 1B:
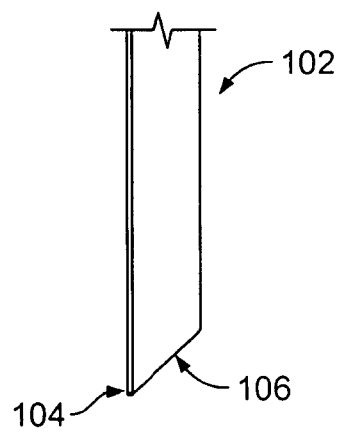
FIG. 1B shows a cross section through a variation of the blade having a single sided support.

FIG. 1B shows a variation of a self-sharpening microsurgical knife 102 having a cutting region 104 supported on a single side by a supporting region 106. As noted above, the cutting region 104 may be clearly distinct from the supporting region 106. Alternatively, it may gradually transition to the supporting material 106.

Figure 1C:
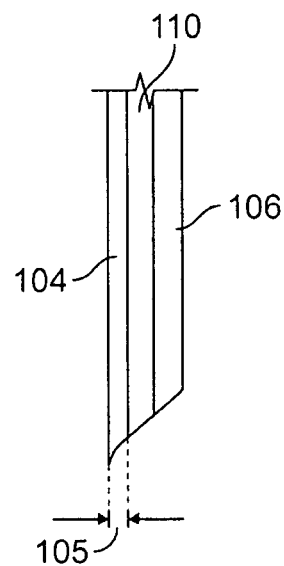
FIG. 1C illustrates a cross-sectional conceptual atomic-level view of a variation of the invention having regions rather than layers of distinct materials.

FIG. 1C illustrates a single sided 102 knife blade having a transition region 110 between the cutting region 104 and the support region 106. As described herein, this variation may have gradual changes in material properties in the different-regions.

The angle 108 adjacent to the exposed cutting region 104 is typically selected during manufacturing of the knife blade and ultimately by the cutting action of the self-sharpening knife during use.

It is noted that the wear rate may be inversely related to the hardness of the material. For example, in some variations of the invention, the material that forms the cutting layer/region and has a lower wear rate may also have a greater hardness than the supporting/transition materials. However, there may be cases where materials having low wear rates are not harder than materials having higher wear rates.

It is noted that in certain variations of the invention the wear rate transitions over a region. Accordingly, it may be difficult to exactly identify a thickness of the cutting region, support region, and/or transition region. Accordingly, as shown in FIG. 1C, a region's thickness may be defined as a span of the region having substantially the same or similar wear rate. For example, a micro-knife of the present invention may have a cutting region having a span 105 of material approximately 500 angstroms thick where this span has a consisting wear rate. The cutting, region may have a transition region on one or more sides that has a non-uniform wear rate. In other words, the nonuniform wear rate transitions from the relatively low wear rate of the cutting region to the higher wear rate of the support region. Such regions may be formed during fabrication of the knife where the same base material forms the support and cutting regions but processing of the materials results in different wear characteristics.

It is noted that in many cases the wear rate of a blade may be held constant over a certain span (e.g., defining a cutting region) but the characteristics of the region change continuously throughout the remainder of the blade. In such variations, there may be no separate transition region and supporting region. Instead, the transition layer functions as a support. Alternatively, the support region may be a span of material having a constant (but higher) wear rate. In any case, the starting and stopping points of the transition between adjacent regions may be difficult to identify.

In any case, the blade edge will be formed by an end of the cutting region (or cutting layer) that becomes exposed through wearing of the support and/or transition region.

The cutting region/layer may be any material that can be formed as a suitably thin film such as diamond, silicon carbide, silicon nitride, boron nitride, boron carbide, tungsten carbide, and many others known in the art. The supporting material may be any material that the chosen cutting material can be deposited on as a thin film with sufficiently low residual stress (or within a specified range of stress so that it does not self-destruct). The supporting material may be single crystal, or it may be polycrystalline, or it may be amorphous. An example of a single crystal material is silicon. Another example is single crystal graphite. An example of a polycrystalline material can also be silicon. An example of an amorphous material is glass (many types of glass may be acceptable). Another amorphous material is vitreous carbon. Polymers (plastic) can also be used. Polymers are usually a combination of polycrystalline and amorphous regions.

Figure 1D:
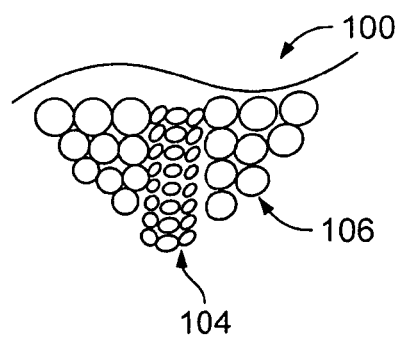
FIG. 1D illustrates a cross-sectional conceptual atomic-level view of a variation of the invention.

FIG. 1D illustrates a cross-sectional conceptual atomic-level view of a double sided microsurgical blade 100. As shown, the minimum thickness of the cutting layer 104 may be as small as a few angstroms (e.g., 4 angstroms). Similarly, the minimum thickness of the adjacent supporting layers 106 can be as small as a few angstroms. It is noted that the upper limits of these thicknesses will be determined based on the intended application of the knife. Moreover, it is noted that the thickness of the supporting layer will decrease as it approaches the blade edge.

In use, the support material 106 wears at a faster rate than the Cutting layer 104. This differential in wear rate maintains a short length of the thin film blade edge 104 protruding from the supporting material 106 so that it can apply the Cutting force to the very small area of the blade edge to provide the high pressure needed for the Cutting to occur.

Ideally the combination of layer widths and properties will be chosen such that the wear rates that occur in normal use will maintain the desired V-shaped profile with the cutting layer at the apex of the V and the support layer material wearing away faster.

One variation of the invention uses single crystal silicon as the support material and amorphous silicon nitride as the cutting material. Two silicon wafers are bonded together. The crystal planes of the two wafers must be carefully aligned so that they will meet precisely at a single line at the cutting edge.

FIG. 2A illustrates the first step in fabricating, devices described herein. This step includes growing a 1 micron thick layer 201 of silicon dioxide (for example, at 1100 degrees C., in oxygen with steam). The oxide is then patterned to provide an etch mask to etch a slot 202 in each wafer 200 to find the crystal planes. In a standard silicon wafer 200, a major flat 205 is in the <110> direction. An etched oriented slot 202 (e.g., oriented 45 degrees) with respect to the flat 205 will have planar vertical sidewalls that are suitable for robustly contacting mechanical alignment pins 210. The etching, must be done with an anisotropic etchant such as aqueous potassium hydroxide (KOH). FIG. 2A shows the 45 degree angle 204 relationship between the etched slot 202 and the major flat 205 of the wafer.

FIG. 2B shows a side view of two wafers 200 on the alignment fixture 208 and aligned by alignment pins 210 sticking through the etched slots 202. The wafers have been pushed into contact with each other. FIG. 2C shows a perspective view of the two wafers 200 on the alignment fixture. The wafers 200 will stick to each other when they are pushed into contact, but to make a strong bond the wafers may be annealed. This can be accomplished, for example, using nitrogen in a furnace at atmospheric pressure at 1100 degrees C. for 1 hour.

Figure 3A:
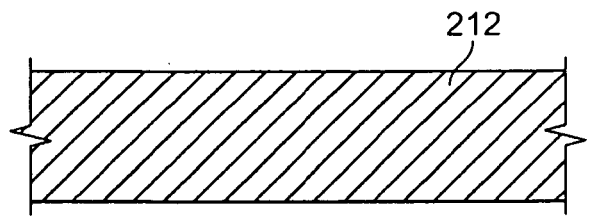
FIGS. 3A-3C illustrate a variation of the steps involved in growing a cutting layer and bonding adjacent Cutting layers together to form a variation of a blade according to the present invention.
Figure 3B:
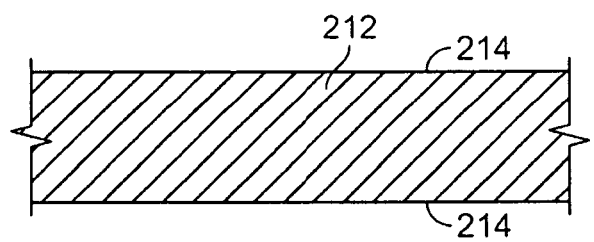
Figure 3C:
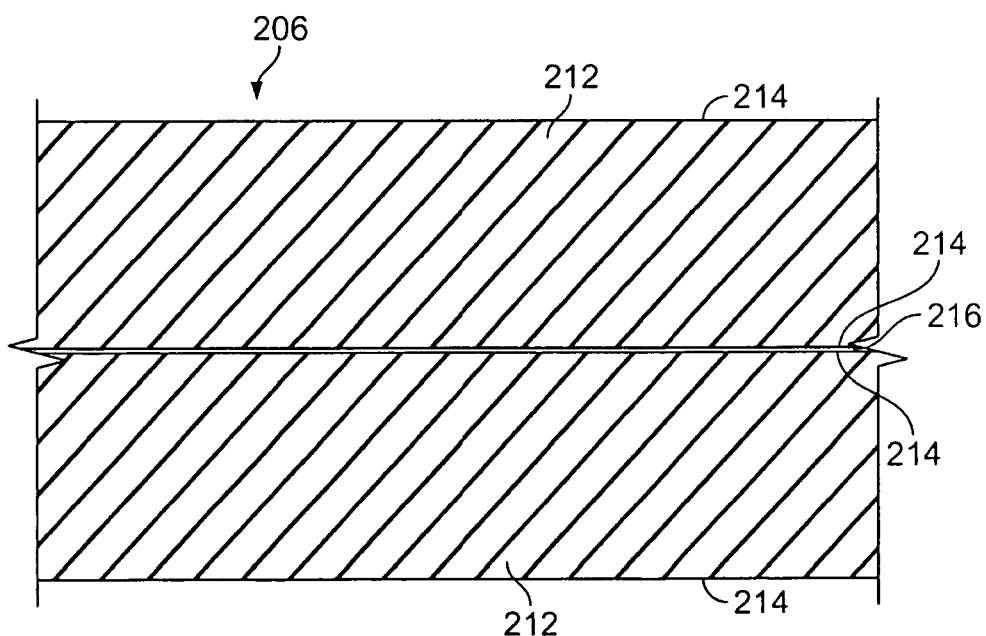

FIG. 3A shows after the alignment slots have been etched, and the oxide layer is removed with concentrated hydrofluoric acid (49 wt % HF in water). FIG. 3B illustrates the next step of growing a thin layer of cutting material 214 (the existing, single crystal silicon 212 being the support or transition region/layer). One example of a cutting material is silicon nitride ($Si_3N_4$). For example, to grow a 25 angstrom thick layer of $Si_3N_4$ the wafers are put in an atmospheric pressure furnace with pure ammonia ($NH_3$) flowing through it at 950 degrees C. for 30 minutes FIG. 3C shows a cross section after two nitride coated wafers 206 have been bonded together to form a combined wafer 206. Before the wafers are bonded they are aligned so that their crystal planes are parallel to each other. The result is a bonded layer 216 of silicon nitride. In another variation, a single nitride coated wafer may be bonded to a bare silicon wafer. This construction permits a sharper edge due to the presence of a single layer of nitride.

Figure 4A:
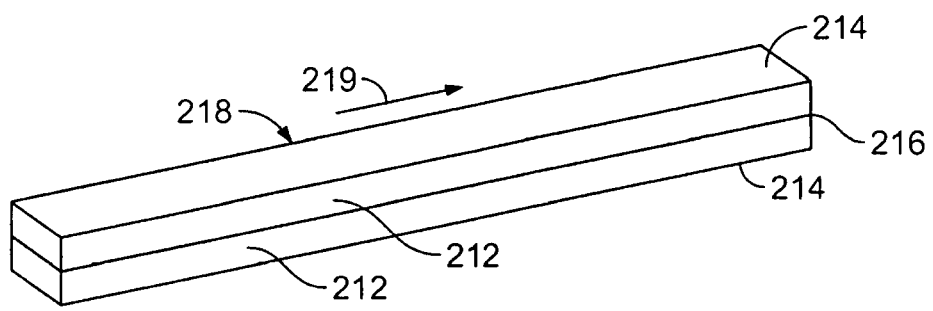
FIGS. 4A-4E illustrate a variation of the steps involved in separating blades from the bonded substrates.

FIG. 4A illustrates the process after the bonding is completed. As shown, the wafers are sawed into bars 218. The long edges of the bars are in the <110> crystal direction 219 (parallel to the major flat of the original wafers).

Figure 4B:
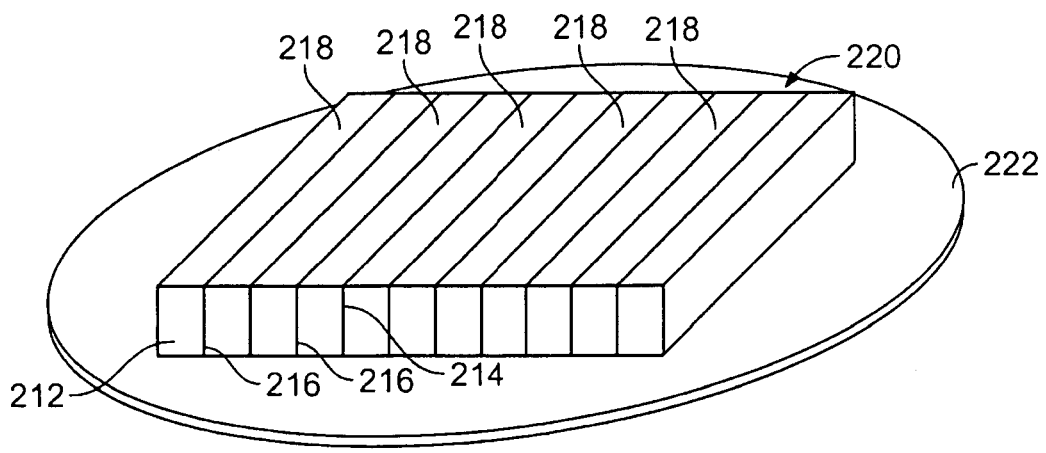
Figure 4C:
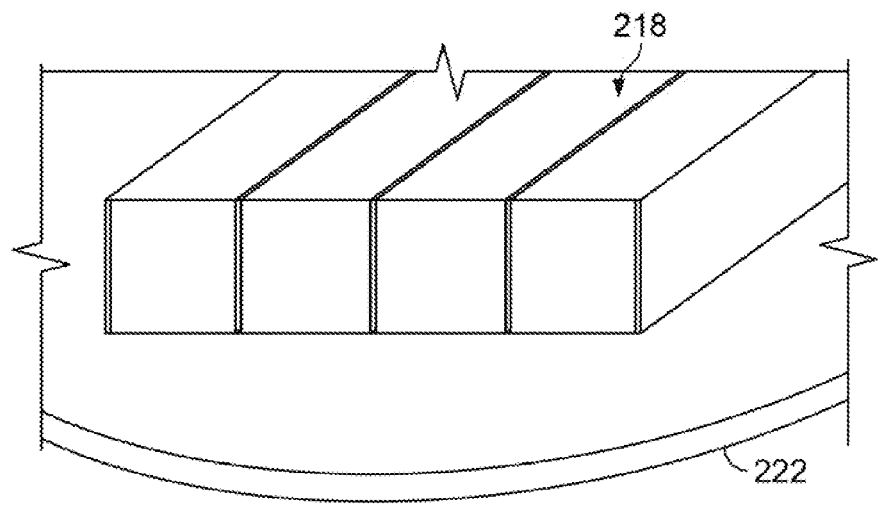

Next, as shown in FIG. 4B, an array of bars 220 are bonded (e.g., using an appropriate glue, or wax) onto a supporting handle wafer 222. The bars 220 are oriented so . that the saw-cut surface is facing up, and the Si3N4 layers are vertical. This allows the sawed face to be lapped flat and polished to a smooth finish. This further allows the cutting layer, and supporting layers to all meet at the same line at the center of each bar. FIG. 4C shows the surface of the bars 218 once polished.

Figure 4D:
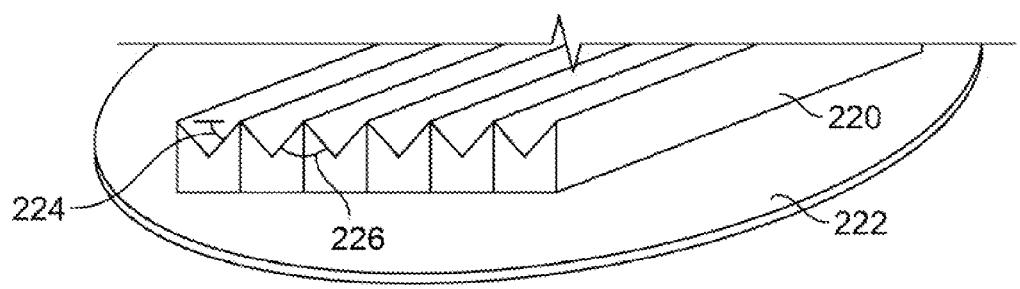

FIG. 4D illustrates the next step of making a V-shaped geometry needed for a knife blade. For example, the bars may be placed in aqueous KOH at 60 degrees C. The silicon nitride is not etched by KOH. The KOH solution dissolves silicon in the <100> direction much faster than in the <111> direction. This produces the V-shaped geometry at an angle 224 of 54.74 degrees. Therefore as a (111) plane becomes exposed to the solution etching stops in the lateral direction and only continues downwards. This produces the V shape with an angle 226 of 70.52 degrees. Note that this angle can be changed by using wafers cut off-angle from (100) as taught in US patent application 2005/013'581 A1 (the entirety of which is incorporated by reference herein).

Figure 4E:
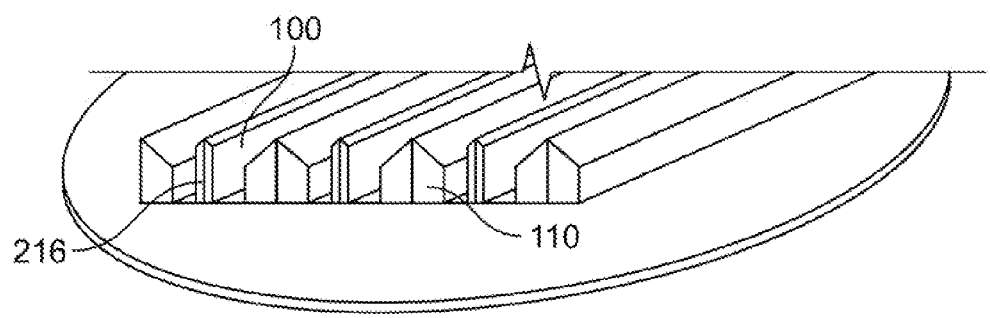

FIG. 4E shows the next step of sawing knife blades 100 to a desired width. Then the knife blades 100 may be sawed to a desired length and individual blades can be removed from the handle wafer. The process leaves scrap 110 consisting of the unbonded but adjacent (contiguous) cutting layers.

FIG. 4F shows a single knife blade 100. If desired, further shaping and smoothing of the sides of blades can be accomplished by lapping and polishing of the blade. For example, the knife blade 100 of FIG. 5A is lapped at an angle along plane 121 to produce a pointed end 112 for the knife blade 100. The end result is the shape shown in FIG. 5B.

Figure 6A:
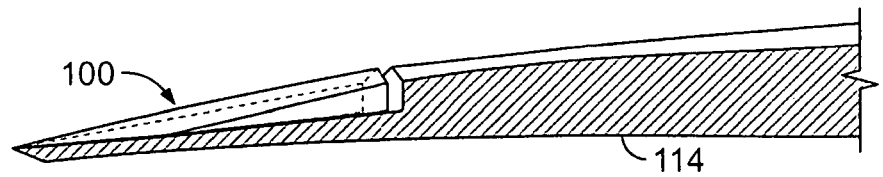
FIGS. 6A-6C illustrate variations of knife blades attached to handles.
Figure 6B:
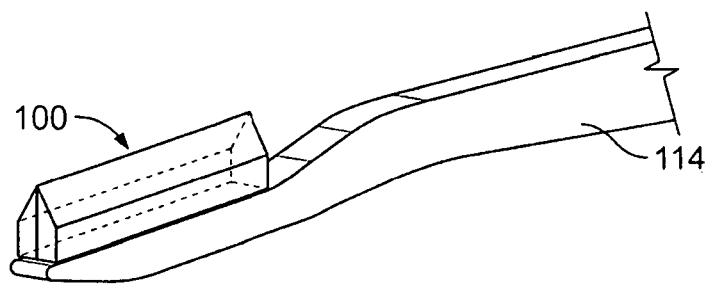
Figure 6C:
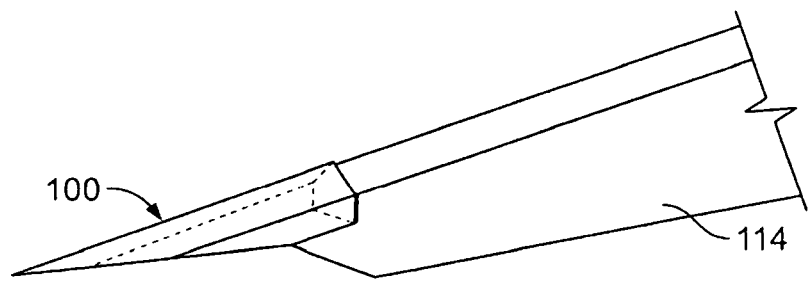

FIGS. 6A-6C illustrates examples of affixing the individual knife blades 100 (for example via glue) onto any desired supporting structure or handle 114 suitable for the intended cutting operation. Alternatively, a blade may be glued onto a handle 114 or fixture for use as a hand held scalpel.

It is noted that the above fabrication steps may be performed with other materials, such as a thin film of silicon carbide grown oil silicon wafers instead of silicon nitride.

The wear rates of the layers of the knife will establish a steady state profile that is dependent on the physical and chemical properties of the material being cut. The original V-shape profile can be restored at any time by dipping the knife in a strong basic solution such as aqueous tetramethyl ammonium hydroxide. This can only be done a limited number of times since the etching will also make the whole knife thinner, but the useful life is quite long since only a fraction of a micron has to be etched away for each sharpening.

Another method for restoring the V profile is to have a specific material for "dressing" the blade (analogous to the traditional process of dressing a dicing saw blade by cutting through a block of material of a certain hardness provided by the manufacturer). The user would restore the blade profile by making a few cuts in the dressing material. This would not subject the sides of the blade to etching so it would not decrease blade life by making the blade thinner. It would only act on the cutting face of the blade, so blade life would be extremely long. The dressing material would have greater stiffness than the tissue normally being cut. Polymers such as silicone, polyurethane, or gelatin, having a desired stiffness can be used. Ion exchange resin can be used to additionally provide a desired basicity by virtue of its bonded —OH groups that react with the silicon on the face of the blade where contact occurs.

Note that it is not necessary to use a crystalline material to create the atomically smooth sidewall slopes by etchings. Since the blades are self sharpening by mechanical wear through normal use, it is only necessary to meet the criterion of having, appropriate wear rate, and be comprised of a combination of materials that is actually manufacturable. For example, a 20 angstrom film of silicon carbide (SiC) can be deposited on a glass wafer (e.g., by sputtering). A thick layer of glass can be deposited on top of the SiC (e.g., by sputtering or diffusion bonding). Bars can be cut from this by sawing, the cutting face profile can be approximated by grinding, and then brought to atomic scale precision by dressing as described above (which is really a form of localized polishing).

Figure 7A:
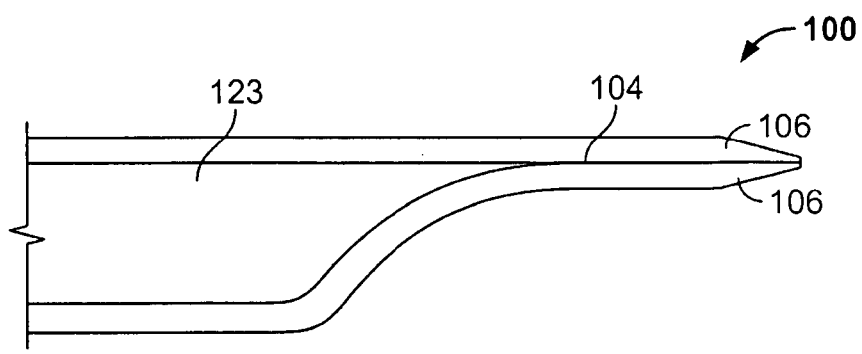
FIG. 7A illustrates a variation of a knife blade having a supporting layer having a varying wear rate where the supporting layer and cutting layer are placed on a substrate.

Another variation of the invention includes a self-sharpening knife with a functional gradient of hardness as described herein. FIG. 7A shows a cross section perpendicular to the plane of the wafer through a microfabricated knife 100. The knife is comprised of a thin layer of cutting layer or region 104 that is mechanically supported by thicker layers/regions 106. Support layers/regions 106 are still considered thin films in normal practical terminology, and cutting layer/region 104 approaches the realm of atomically thin. Layers/regions 106 wear at a greater rate than material 104. The wear rate of layers/regions 106 increases relative to the distance from layer/region 104. As noted above, the wear rate may vary through the device. For example, the wear rate of layers/regions 106 increases with distance from material 104. For example, material at locations closer to the cutting region 104 may wear more slowly, than material at the exterior of the knife 100. Moreover, the layers 104, 106 can be supported by a substrate. FIG. 7A also illustrates the device as having a porous section 123 and channel for delivery of materials as described below.

Example systems are:

| material at 104 | (material at 106) | (material between 106 and outer surface) | (material at outer surface) |
|---|---|---|---|
| diamond | SiC | $SiC_{(1-f(x))}$ | Si |
| $Si_3N_4$ | $Si_{(3+g(x))}N_{(4-f(x))}$ | $Si_{(3+g(x))}N_{(4-f(x))}$ | Si |
| SiC | Si | Si of increasing porosity | Si with greatest porosity |
| $Si_3N_4$ | Si | Si of increasing porosity | Si with greatest porosity |
| Diamond | Si | Si of increasing porosity | Si with greatest porosity |

Note:
f(x) and g(x) are monotonically increasing functions of the distance (x) from the cutting layer Porous silicon is made by photoelectrochemical etching of lightly to moderately doped n-type silicon in dilute hydrofluoric acid (e.g., 5% aqueous HF). The diameter of the pores increases with increased electrical current density during etching. Therefore the fraction of porosity in the material can be decreased as the etch progresses towards film 104 by programmed decrease of the electrical current as a function of time. The wear rate will be highest where the porosity is greatest since there is less solid material there. The wear rate will decrease as the porosity of the material decreases. The porous material can be filled with lubricant and/or biologically active chemicals, such as medicines, proteins, or DNA. A photolithographically defined mask can be used to limit the areas of photoelectrochemical etching to only those regions where knife edges, fluid reservoirs and fluid conducting channels will be. Porous silicon may also be made using p-type silicon and electrochemical etching in an HF solution (no light required for p-type silicon). The porosity of the silicon may be adjusted based on the applied current density.

A silicon carbide film can be deposited with a programmed increase in the fraction of the silicon supplying material and/or decrease in the carbon supplying material during the course of the deposition such that the resulting film has the desired composition as a function of distance from the film 104. For example, stoichiometric SiC could be deposited on the surface of film 104, and then the fraction of silicon supply could be increased by 0.1% and the carbon supply decreased by 0.1% per Angstrom of film deposition so that after the film is 1000 Angstroms thick, only pure silicon is being deposited. An example of a deposition process that may be used for fabrication of devices described herein is "low pressure chemical vapor deposition." This process allows for acceptable angstrom level control needed for depositing uniform films of covalently bonded materials (such those described herein) that can then be formed by typical micromachining processes.

Similarly for silicon nitride, the film can be deposited with a programmed increase in the fraction of the silicon supplying material and/or decrease in the nitrogen supplying material during the course of the deposition such that the resulting film has the desired composition as a function of distance from film 104. For example, stoichiometric Si3N4 could be deposited on the surface of film 104, and then the fraction of silicon supply could be increased by 0.1% and the nitrogen supply decreased by 0.1% per Angstrom of film deposition so that after the film is 1000 Angstroms thick, only pure silicon is being deposited.

Not only silicon, but any material that can be processed to have a gradient in porosity could be used for the construction of a self-sharpening knife.

Figure 7B:
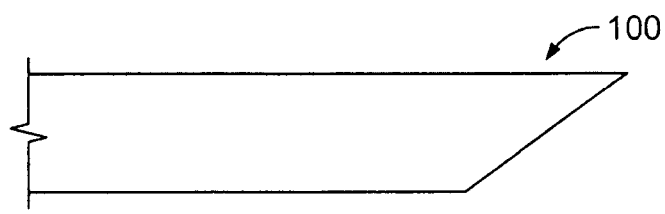
FIGS. 7B-7D and 8A-8D illustrate various shapes of knife blades according to the present invention.
Figure 7C:
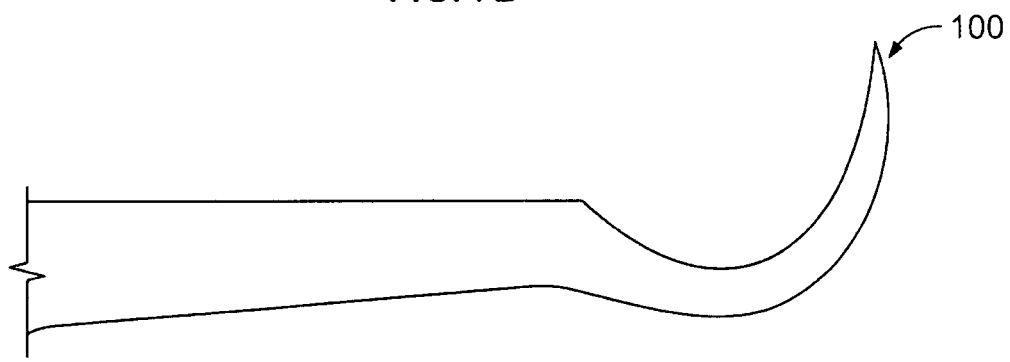
Figure 7D:
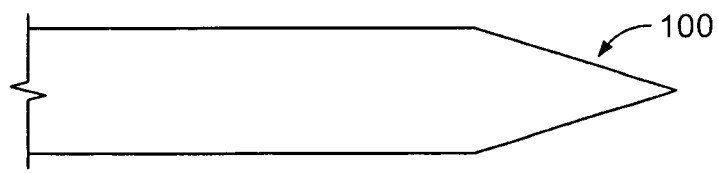

FIGS. 7B-7D show example plan views of knife designs. Essentially any 2 dimensional shape that can be drawn can be made if desired for a particular application. For example, when viewed in 2 dimensions the shape may be continuous or may have openings within the 2 dimensional shape. It should be understood that any such shape and/or profile is within the scope of this invention. Additional shapes are shown below.

Figure 8A:
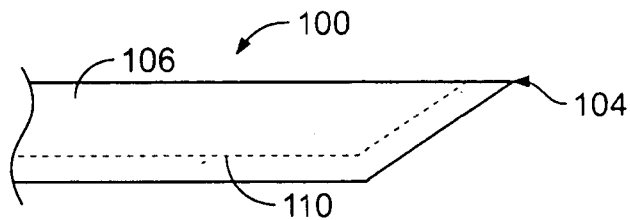
Figure 8B:
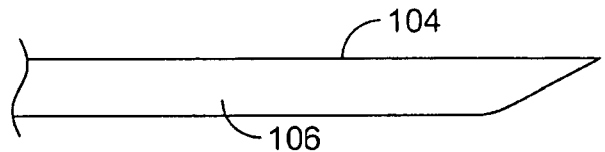

FIGS. 8A-8B show cross sections through single sided designs 102 having supporting material on only one side of the cutting layer/region 104. In FIG. 5A the supporting region 106 is single crystal silicon that has been partially etched to produce a zone of gradient porosity 110. The cutting edge 104 extends from the ends of the knife 100.

FIG. 8B shows a thin cutting film 104 supported on one side by a layer of material 106 whose wear rate increases with distance from film 104.

Figure 8C:
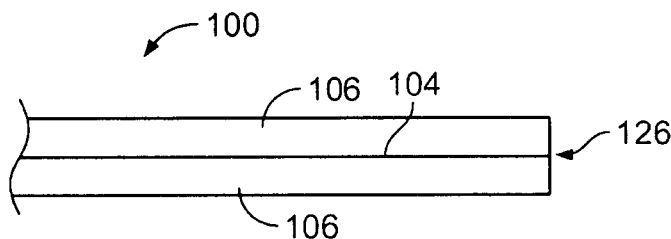
Figure 8D:
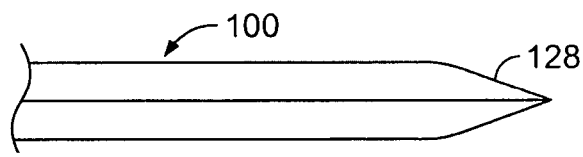

FIG. 8C shows a cross section of a structure comprised of an atomically thin cutting film 104 between two layers of supporting material 106 (e.g., single crystal silicon). The silicon layers may be photoelectrochemically etched to have a porosity that increases with distance from the cutting film 104. In FIG. 8C the knife 100 is shown as-etched, with a blunt edge 126. FIG. 8D shows the structure 100 with a sharp or tapered 128 edge produced by wearing away the support material (i.e. silicon layers (106) by making cuts in sheets of material of suitable hardness.

Figure 8E:
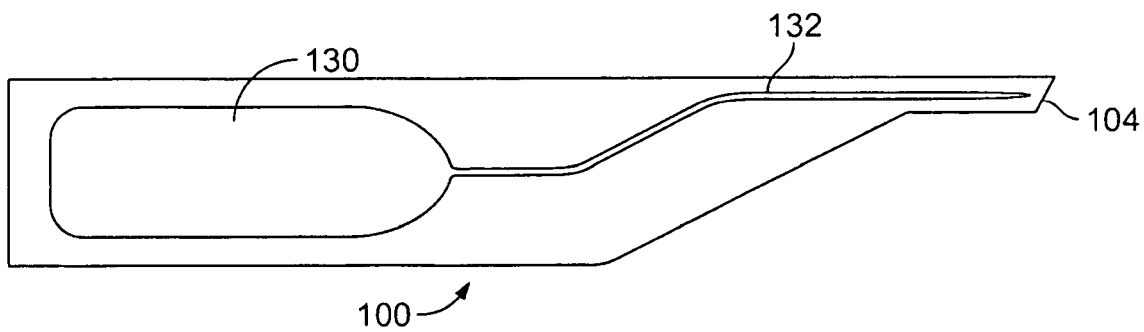
FIG. 8E illustrates a variation of a knife blade according to the present invention where the knife blade includes a reservoir and one fluidic channel.

FIG. 8E illustrates a knife 100, reservoir 130, and fluidic channel 132 that extends to, or near the cutting edge 104. The reservoir 130 and/or channel 132 can be etched or otherwise manufactured. The reservoir 130 can be filled with lubricant and/or biologically active treatment(s), and the channel(s) can conduct the fluid(s) (which may contain suspended particles) at a predetermined rate to the cuttings edge along which they will spread by diffusion and be transported to the cells that are being cut. Any particles and chemicals that do not have the ability to penetrate an intact cell membrane will only affect the cells whose membranes have been cut. Particles and chemicals that do have the ability to penetrate cell membranes will also affect intact cells, but only in the very confined region that has been touched by the knife.

Note that any materials that can be patterned by etching (e.g., silicon, porous silicon, silicon nitride and silicon carbide) can have integrated reservoirs and fluidic channels.

Other commonly known MEMS elements can be integrated with the design, such as flexures, actuators, electrodes, etc. The art for doing this is especially well developed for silicon, but other materials can be used within constraints.

Figure 9A:
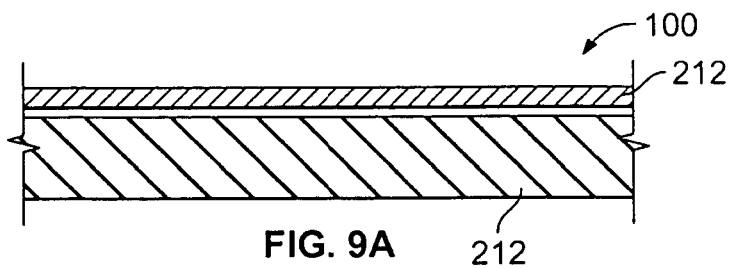
FIGS. 9A-9G illustrate an example of a single sided process of forming a blade.

FIGS. 9A-9G illustrate an example of a method for fabrication of a single-sided self-sharpening microknife. The steps are described as follows. FIG. 9A illustrates cleaning a silicon on insulator (SOI) wafer 160 having (100) orientation.

Figure 9B:
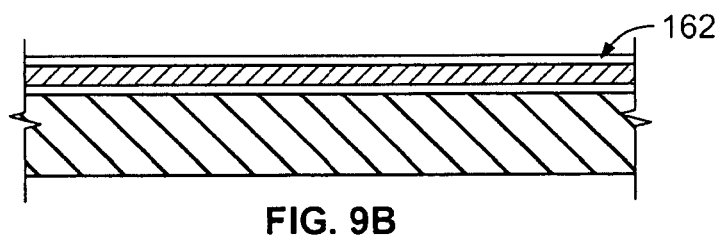

FIG. 9B represents growing 1 micron thick thermal oxide 162, wet oxidation, 1050 degrees C., for 1 hour.

Figure 9C:
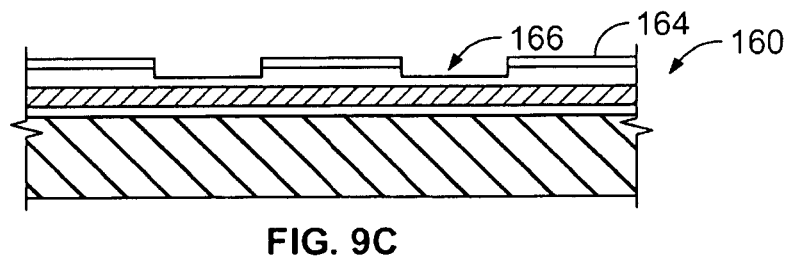

FIG. 9C shows a spin application of a photoresist 164 to the front side of the wafer 160, patterning of the photoresist 164 to form the knife structures (mask 1) and then submerge wafer in 5:1 buffered hydrofluoric acid for 4 minutes to thin the exposed oxide 166.

Figure 9D:
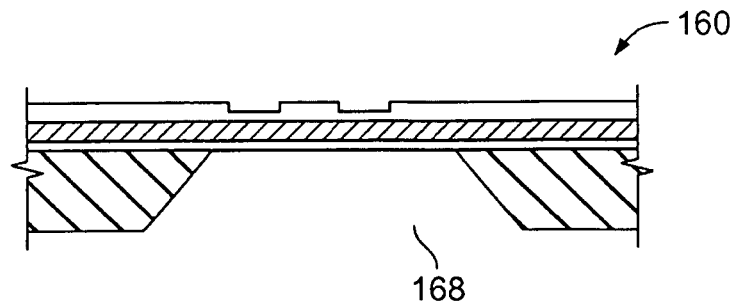

FIG. 9D illustrates the assembly after a spin application of photoresist to the front side of the wafer 160 to protect from handling damage spin apply photoresist to back side of wafer. Next, spin application of photoresist to the back side of the wafer 160. The back is patterned for die release cavities 168 (mask 2). The pattern is aligned to the front side pattern and a 5:1 buffered hydrofluoric acid is applied to the back side to remove exposed oxide (about 5 minutes). Next, all of the photoresist is cleaned off, the backside die release cavity is etched (TMAH, 80 degrees C., about 7 hours) producing the profile shown.

Figure 9E:
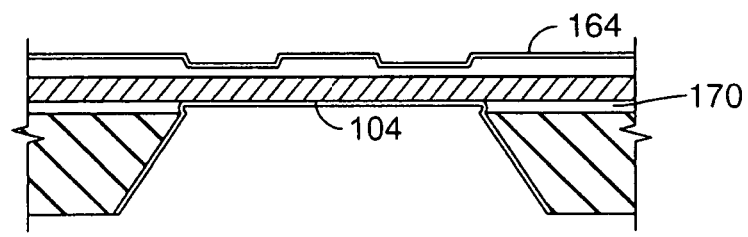

FIG. 9E shows the wafer 160 after a spin application of photoresist 164 on the front side of wafer 160 is applied for protection. Next, a 5:1 buffered hydrofluoric acid is applied to the back side to remove the exposed buried oxide layer 170. A cutting film is deposited. As noted above, the cutting film 104 has low wear rate (e.g., SiC, $Si_3N_4$, low stress silicon nitride, or diamond), with desired thickness (e.g., 10 angstroms to 100 angstroms).

Figure 9F:
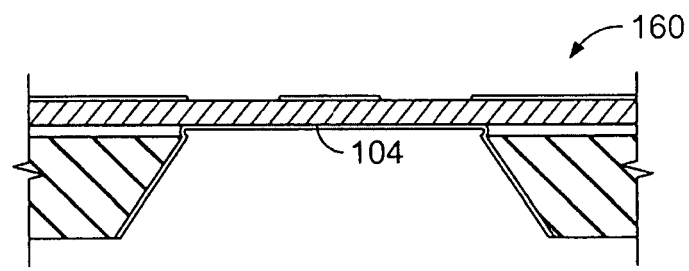

Next, as illustrated by FIG. 9F, a photoresist is spin applied to the back side of the wafer 160 to protect the cutting layer 104. Then, the cutting layer material 104 is removed from the front side of the wafer 160 by etching (e.g., $SF_6$/He plasma, 100 watts, 30 seconds, or oxygen plasma if cutting film is diamond). Next, a 5:1 buffered hydrofluoric acid is applied to the front side of the wafer 160 for 5 minutes to remove thin oxide. However, this leaves about 0.5 microns thickness of oxide that was previously patterned in step 4. Finally, all of the photoresist is removed.

Figure 9G:
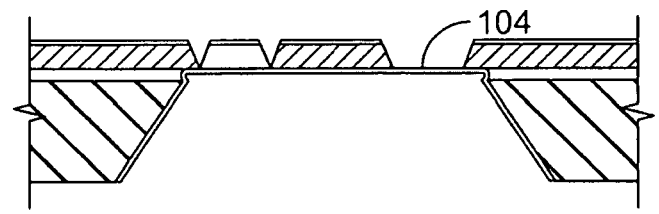

FIG. 9G shows the etching of the exposed silicon in TMAH (e.g., 12 wt % aqueous 80 degree C.) to reveal cutting layer 104 from the front side. Next, each individual knife blade can be attached to a handle (e.g., by gluing or other method) and the knife blade may be conditioned mechanically (e.g., by cutting a predetermined length and depth of material having, wear rate suitable for the intended application, such as a 24 durometer polyurethane. The knife may be conditioned chemically as well.

Figure 10A:
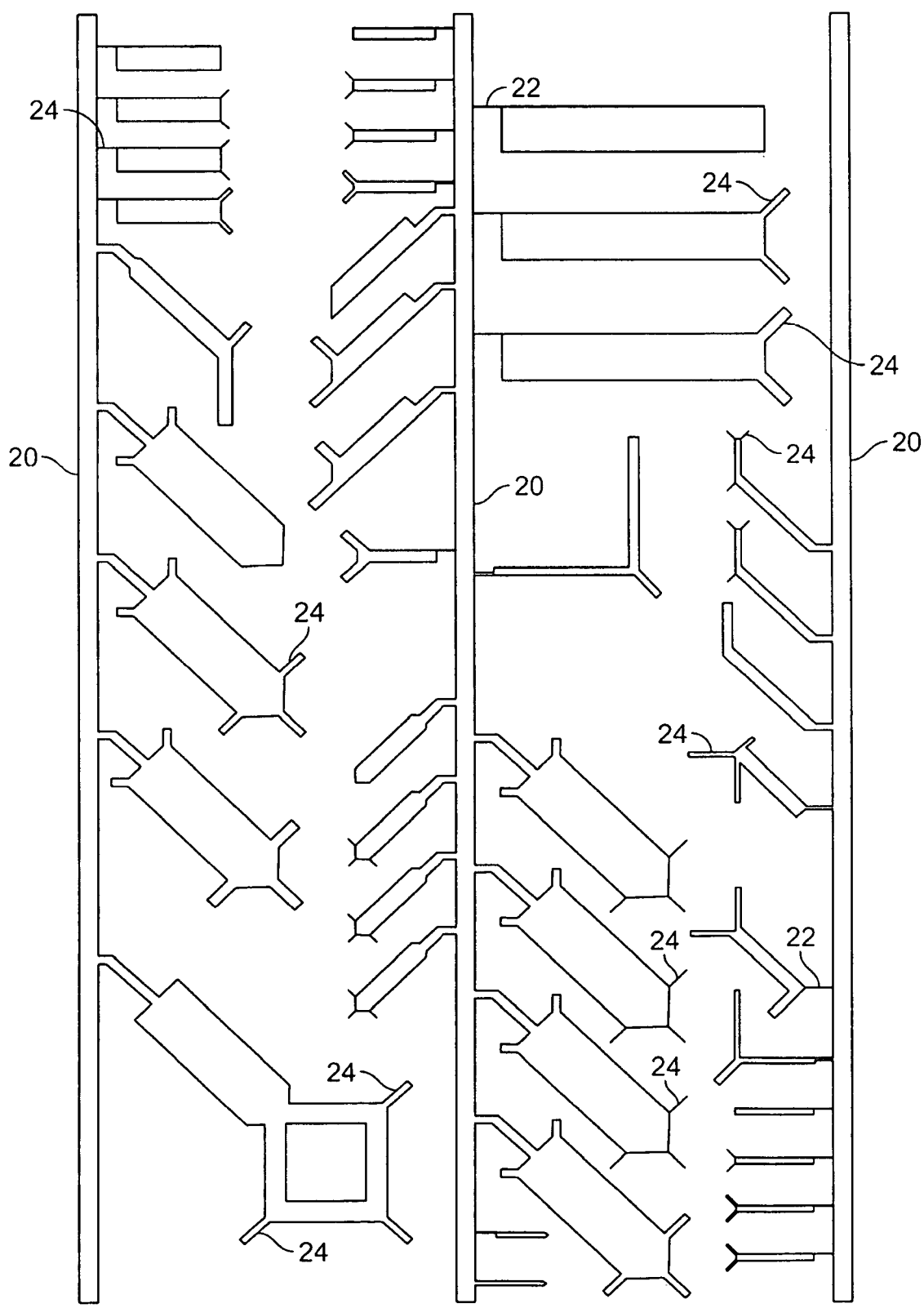
FIG. 10A shows a variation of a mask layout used to make microknives illustrated in FIGS. 12A-12D.

FIG. 10A: shows a variation of a mask layout used to make microknives illustrated in FIGS. 12A-12D. In this example, the layout was made in (100) oriented silicon, so all vertical and horizontal edges of the pattern produce sharp cutting edges. All 45 degree edges make vertical walls. The long vertical bars 20 extending the full height of the figure are support beams that hold the parts in place after the etch so they do not float away.

FIGS. 10B-10D show various aspects that may improve the final construction of the knife. Thin tether beams 22 hold the finished parts to the support beams 20. In use, a microgripper can grasp a microknife blade and pull it away from the support beam (breaking the thin tether beam 22) and carry it to the suspension for mounting of the microknife. FIG. 10C shows corner compensation patterns 24 used to keep the corners from etching away. FIG. 10D shows how the 45 degree corner compensation patterns 24 etch away while preserving the sharp corners or cutting edge 104. Preferably, the etching process should be terminated.

While the subject knives may be used as surgical microknives, it is understood that they will have other applications. For example, as shown in FIGS. 10E-10G, any of the described knives may function as scrapers to remove contamination from a photolithographic mask. And more generally, the micro-blades may clean any smooth surface. In particular, the problem of submicron particles and contamination on photolithographic masks used in the production of integrated circuits is solved by using this tool.

Figure 11A:
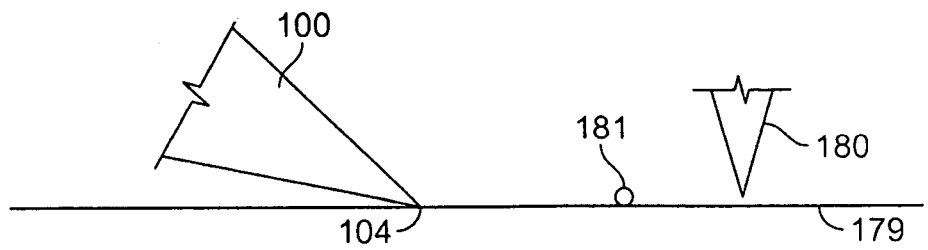
FIGS. 11A-11C show the image the process of cleaning of masks used in the production of integrated circuits.
Figure 11B:
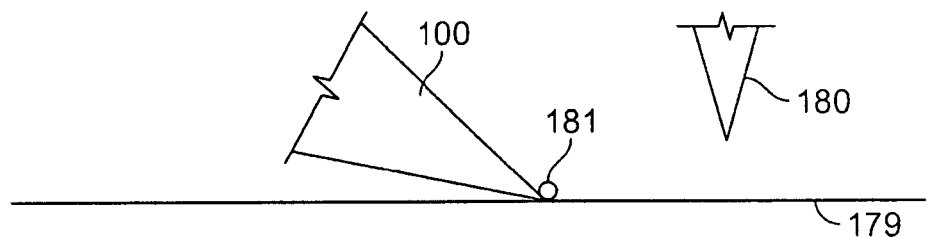
Figure 11C:
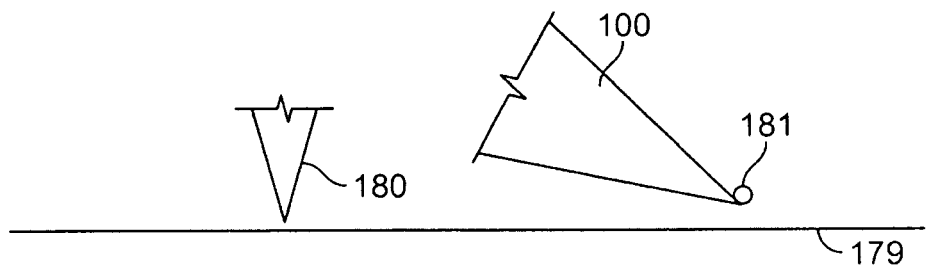

FIGS. 11A-11C shows the process of cleaning masks 179 used in the production of integrated circuits. In such a process a scanning probe microscope, such as an atomic force microscope, (AFM) can be used to watch both the edge of the knife 100 and the contamination 1 that is being removed. A scanning probe microscope can resolve much smaller features than an optical microscope can (although this scraper tool can be used with an optical microscope as well, if desired, to address particles larger than 0.1 microns). For use as a cleaning tool, the knife edge 104 should have a chemical treatment to make it sticky (just stickier than the surface being cleaned) so it will trap the dirt. It is important to note that the thinness of the knife edge 104 allows it to get under submicron particles 181, and lift them away from the surface to be cleaned. A knife 100 in the shape of a chisel may be a preferred tool shape for this application.

FIG. 11A illustrates an example in which an AFM 180 finds a particle 181. The AFM 180 rasters over the area to create an image of the particle, mask surface and blade edge, so the controlling computer knows the relative locations of the items.

FIG. 11B illustrates a step where a computer directs the micropositioning stages to move the knife edge 104 under the particle 181.

FIG. 1 IC shows the computer directing the micropositioninig stages to lift the knife edge 104 away from the surface. It can then go to a cleaning station, or continue in use and just keep accumulating particles.

The AFM can produce another image at any time during the process, or just wait until the end to verify that cleaning was successful.

Figure 11D:
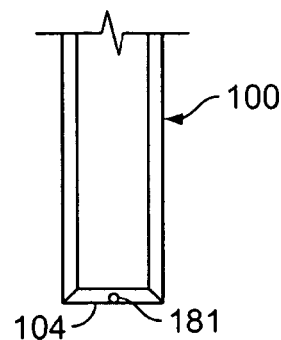
FIG. 11D shows the removed particle stuck to a blade edge.
Figure 12A:
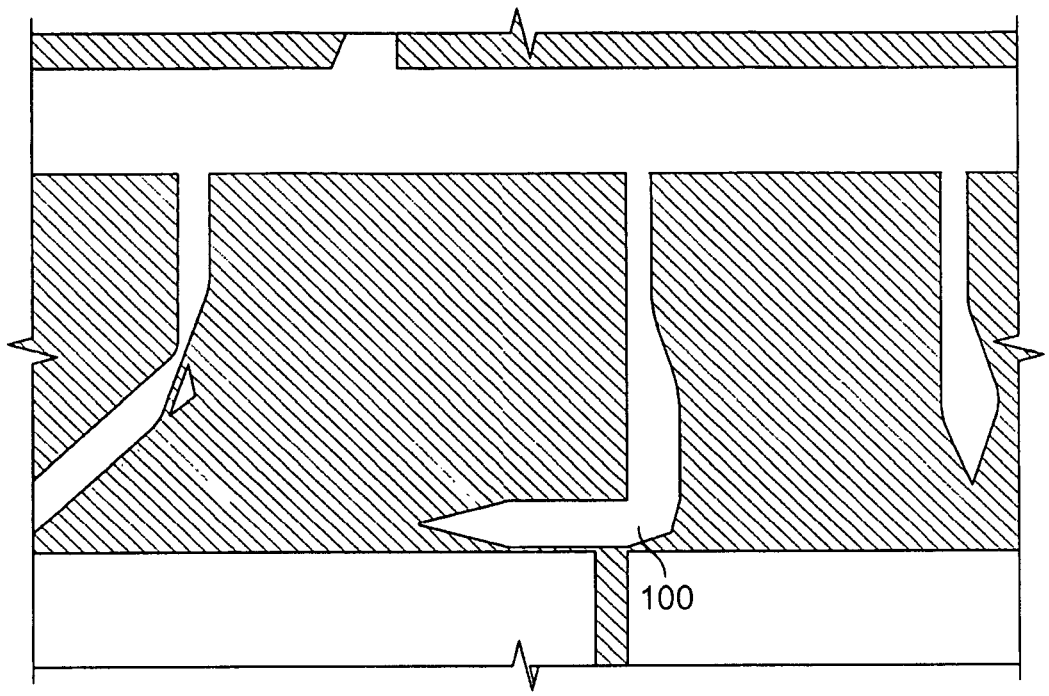
FIGS. 12A-12D illustrate additional examples shapes of micro-knives according to the present invention.
Figure 12B:
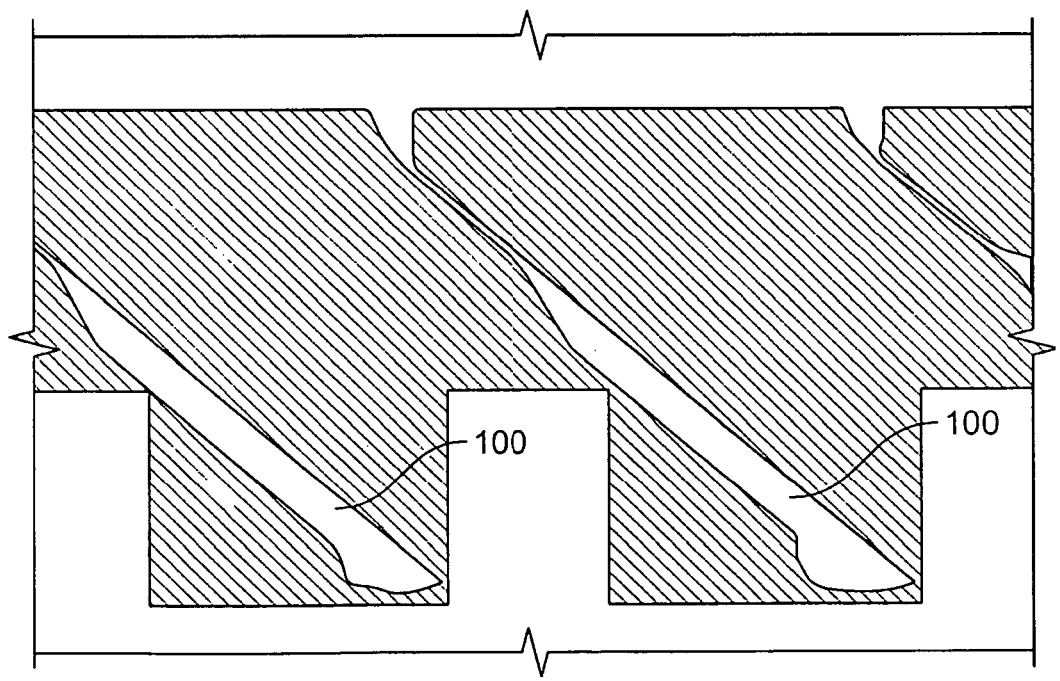
Figure 12C:
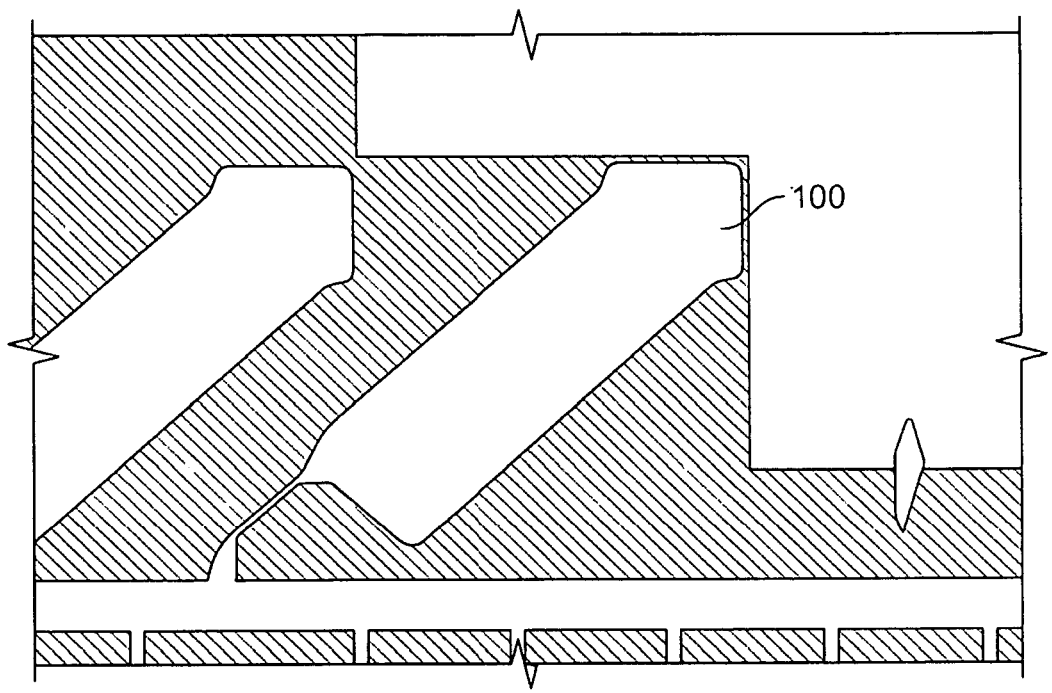
Figure 12D:
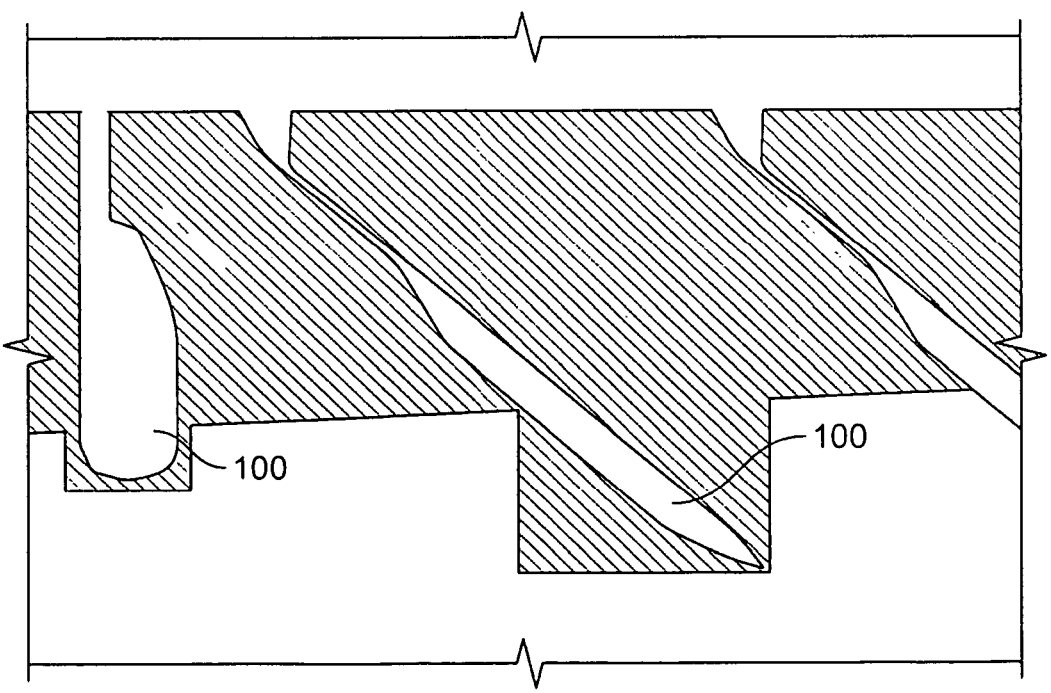

The knife is mounted on a compliant suspension that holds the scraping edge in contact with the surface of the full length of the scraping edge, and within a predetermined range of force. FIG. 11D shows the removed particle 181 stuck to the blade 100 edge 104.

Although the silicon wafers have features such as flats or notches ground in them to locate the direction of the crystal planes, this is not done accurately enough for obtaining the best possible structures. In best practice, the first step in processing should be to etch a crystal direction finding pattern (e.g., using the method of Vangbo, et. al. *Precise Mask Alignment to the Crystallographic Orientation of Silicon Wafers Using Wet Anisotropic Etching*, J. Micromech. Microeng. 6 (1996) 279-294, the entirety of which is incorporated by reference.) The features etched in the wafer by this procedure can then be used to accurately align the mask that defines the knives with respect to the crystal plane directions.

FIGS. 12A-12D illustrate additional examples shapes of micro-knives according to the present invention as created with the mask of FIG. 10A.

FIGS. 13A-14C illustrate another example of a process to make blades in which the hard cutting layer is supported on both sides by a material having a relatively higher wear rate (such as silicon).

Figure 13A:
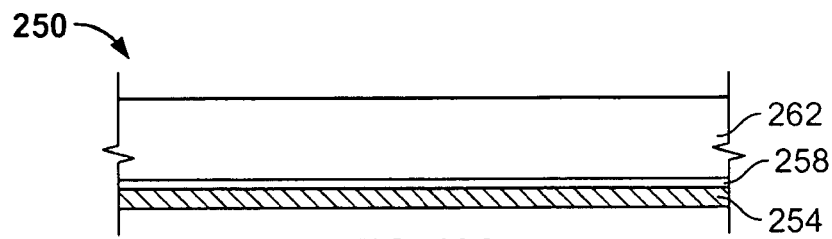
FIGS. 13A-14C illustrate a process for fabricating double sided knives according to the present invention.
Figure 13B:
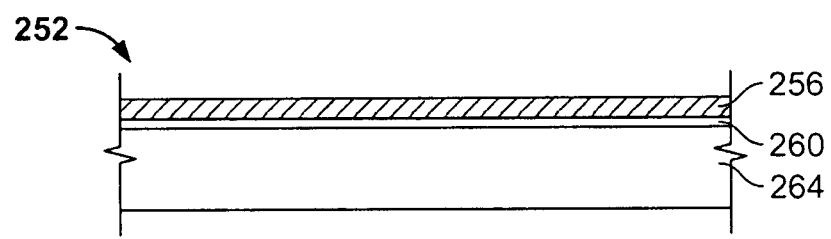

FIGS. 13A and 13B illustrate a first wafer 250 and a second wafer 252, where each wafer comprises silicon on insulator (SOI). The first wafer 250 and second wafer 252 have a device layer 254, 256 thickness that may range anywhere from 5 microns to 50 microns. In one example the thickness of device layer 254, 256 is 20 microns. A layer of buried oxide (BOX) 258, 260 is beneath the respective device layers. The BOX layers 258, 260 may have a thickness anywhere from 0.1 microns to 1 microns. In the present example, the layer is 0.5 microns in thickness. Next, the wafers 250, 252 have handle layers 262, 264 ranging from 200-600 microns thick in the case of a 100 mm diameter wafer.

Next, the device, layers 254, 256 of the wafers 250, 252 are patterned to find the crystal direction. Accordingly, they are etched in KOH to determine the direction of the crystal plane. After determining the direction of the crystal plane, a layer of nitride 266 is grown on the first wafer 250 only. The thickness of the nitride layer 266 may range from 10 angstroms to 500 angstroms.

Figure 13C:
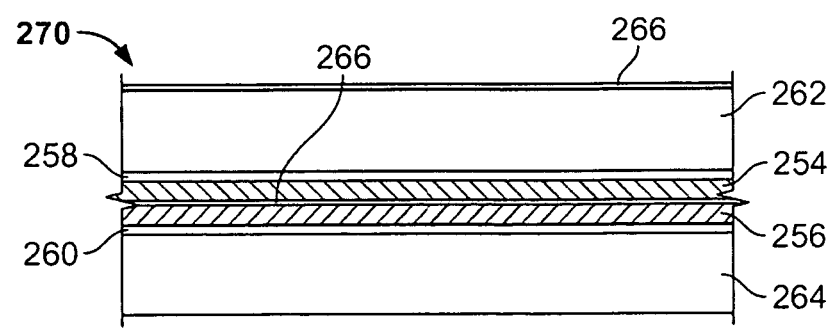

Finally, as shown in FIG. 13C, the first wafer 250 with the nitride layer 266 is bonded to the second wafer 252 with the crystal planes of the wafers being aligned. A wafer aligner/bonder may be used to align the crystal planes of the two wafers 250, 252 and bond them together to produce the layers. Accordingly, the bonded assembly 270 now comprises a first handle 262, a first BOX layer 258, a first device layer 254, a nitride layer 266, a second device layer 256, a second BOX layer 260, and a second handle layer 264. One possible method for bonding the wafers together includes a high temperature bonding using such options as: (annealing in nitrogen at 1050), or (growing about 0.5 micron oxide, 1050 C, in steam).

Figure 14A:
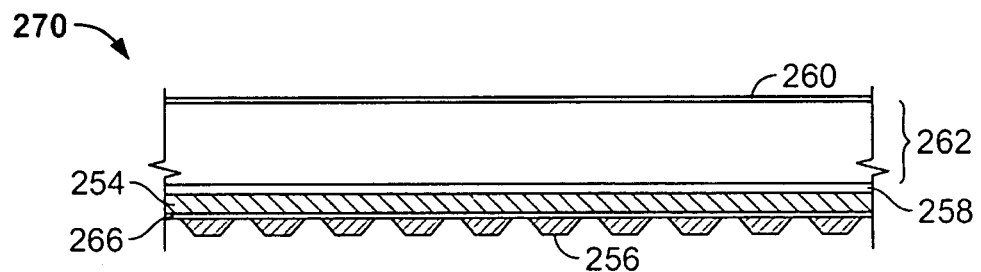

Next, as shown in FIG. 14A, any oxide layer is removed from the exposed side of the second handle layer 264 (e.g., removing the oxide with aqueous HF). The second handle layer 264 is also removed (e.g., with aqueous TetraMethyl Ammonium Hydroxide, TMAH). A photo resist is applied and the second BOX 260 is patterned for defining one side of the knives. The second device layer 256 is then etched using aqueous KOH, or TMAH leaving the assembly 270 shown in FIG. 14A.

Figure 14B:
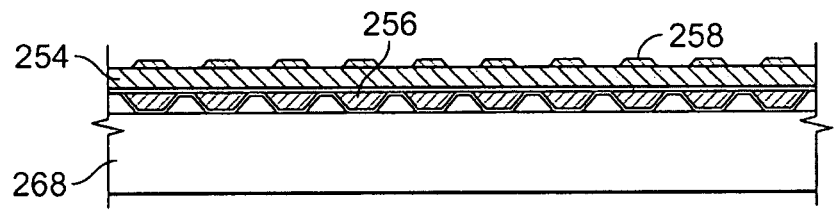

Next, as shown in FIG. 14B a 0.1 micron layer of oxide (1050 C, steam) is grown on the assembly 270. The assembly 270 is bonded to a new handle layer 268. Next, another layer of 0.5 micron oxide (1050 C, in steam) (or anneal in nitrogen 1050 C) is grown. Then, any oxide and nitride is removed from the exposed area of the first handle layer and the first handle layer is then removed (e.g., using aqueous TMAH).

FIG. 14B shows the assembly 14. The third handle layer 268 is patterned. The knives 100 may be located using an IR through-wafer aligner to see buried knives, and etch to box 2 with TMAH to make die site windows. This step can be performed using anisotropic plasma etching and grayscale lithography to produce stress reducing fillets in the silicon. The first BOX layer 258 is patterned using front-to-backside aligner to align the first device layer 254 with the second device layer 256.

Figure 14C:
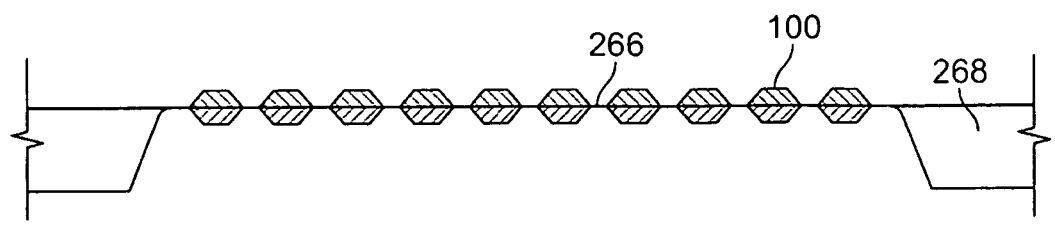

FIG. 14C illustrates the first device layer 254 as being etched through to the nitride layer 266 (using aqueous KOH or TMAH). This process leaves the knife body 100 still attached to the third handle layer 268 via the nitride layer 266. Finally, the oxide is stripped from the knives 100 (e.g., using HF). The knives 100 are ready for mounting onto handles or other fixtures for use. Yet another way to make microknives is to use chemical mechanical polishing (CMP). CMP is a standard process in the fabrication of integrated circuits on silicon wafers. In particular, the chemistry used in the slurry to polish silicon, and stop on a thin layer of silicon nitride can be used to process the microknives for sharp cutting edges. In this process silicon is removed relatively faster than nitride. Therefore as silicon wears away to expose areas of nitride, the nitride wears away at a much slower rate. Accordingly, the whole area of a wafer assembly 270 can reach a state where is silicon removed to a desired depth. In the same way, with a knife edge made of a thin layer of nitride supported by a layer of silicon, the CMP process can form a taper in the silicon to make a cutting edge and stop when the nitride is exposed. However, a difference is that the knife blade will be angled to the polishing surface. It is important that the CMP process insures that only very low forces are applied to the knife edges since they are very fragile towards the edge given the atomic scale of the knives. As a result, a low force, low inertia CMP apparatus should be used. This strategy eliminates the need for alignment to crystal plane directions, so different knife shapes can be made (for example, curved blades).

Next, the mounting region of the blade is processed. Long knife blades (i.e., where a blade length is significantly greater than blade thickness) are vulnerable to being broken off at the base where they are mounted to the handle. The fabrication process can leave atomically sharp flaws such as scratches and cracks. Such flaws concentrate the stress due to applied forces, and can increase the probability of fracture. To eliminate or reduce these flaws, an isotropic etch may be performed on the assembly 270. Since the isotropic etch removes material in all directions, sharp defects become rounded and blunt. This greatly reduces the concentration of stress, diminishing it by spreading it throughout a large volume of material. However, it is important to protect the cutting edges during the isotropic etch process since the cutting edges need to remain sharp. In one example, a knife blade can be dipped into photoresist to a predetermined depth to protect the Cutting edges. The photoresist is then hard baked. The exposed base of the knife blade is then etched isotropically (e.g., $SF_6$ plasma) for a sufficient time to remove approximately 0.1 micron to 1.0 micron of silicon. Next, the photoresist can then be removed, and the knife may be mounted on a handle.

Figure 15:
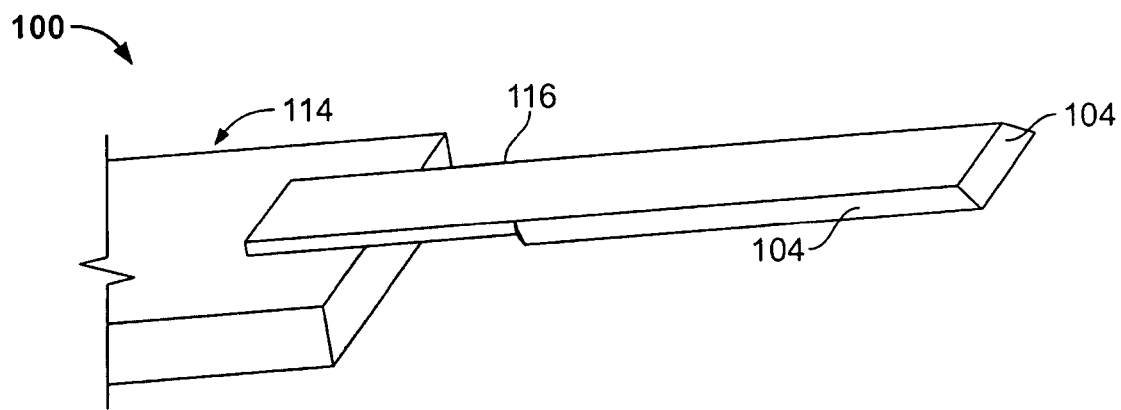
FIG. 15 shows a micro knife that has been processed at its base to remove stress concentrating flaws such as cracks and scratches.

FIG. 15 shows a microknife 100 mounted (e.g., by gluing) on a support base or handle 114. The base region 116 of the knife 100 has undergone isotropic etching to remove flaws. The cutting region 104, having been protected, remains sharp.

Figure 16A:
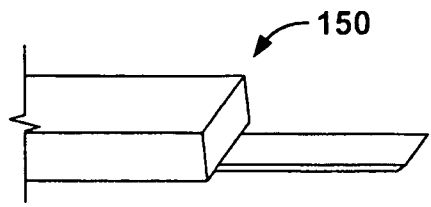
FIGS. 16A-19B show variations of mounting geometries for knives according to the present invention.
Figure 16B:
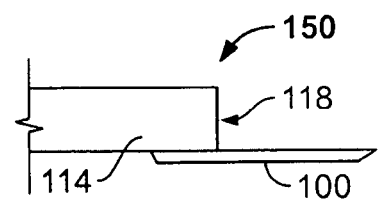

Another stress concentrator in the knife handle 150 assembly is the transition region from the exposed knife blade 100 to the attachment point on the mounting structure 114. FIGS. 16A and 16B show perspective and side views of a knife-handle assembly 150. In the variation of FIGS. 16A and 16B, the blade-handle interface region 118 is a sharp corner. The stress generated in the blade as a result of bending concentrates in the sharp corner given the small volume of blade material at the corner. This configuration may result in increased breakage of the blade 100. However, in some variations, this configuration may be desired.

Figure 17A:
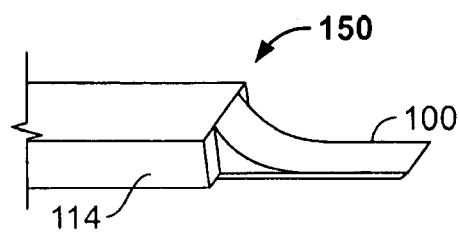
Figure 17B:
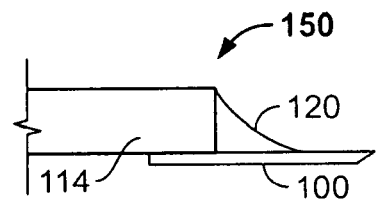

FIGS. 17A and 17B illustrate perspective and side views of a knife-handle assembly 150 having a interface region 120 of increased volume. Such a fillet geometry distributes bending stress through a larger volume as compared to the variation in FIGS. 16A and 16B. Accordingly, the magnitude of stress is relatively reduced. The filet 120 may be constructed from etched silicon, or reflowed glass, or a polymer such as epoxy.

Figure 18A:
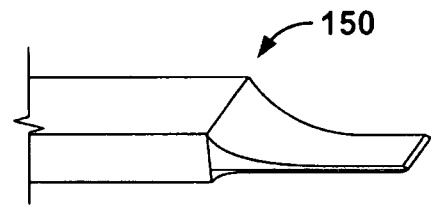
Figure 18B:
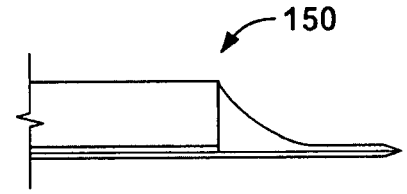

FIGS. 18A and 18B also illustrate perspective and side views of a knife-handle assembly 150 with all surfaces of the interface region being filleted to increase the volume at the transition region.

Figure 19A:
Figure 19B:
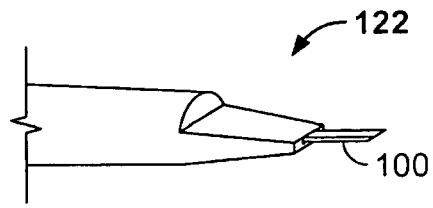

FIG. 19A illustrate a handle or catheter 117 suitable for use via a medical practitioner. FIG. 19B illustrates a magnified view of the end of FIG. 19A showing a microknife 100 mounted on the tip of the handle.

Rather than just dissolving away the handle wafers of the SOI Construction as described above, an option is to etch additional useful structural features from the handle layer. Two-sided processing of SOI wafers can be used to produce useful mounting features in the "handle" layer, in addition to the knife blades in the "device" layer. Possible features in the handle layer include alignment surfaces for assembly to other mounting Structures, and fillets. Fillets that vary in thickness in the direction perpendicular to the plane of the wafer may be produced by "grayscale" lithography which produces a sloping material thickness as a function of position as defined by the grayscale mask. The fillets in the variations shown herein can be fabricated by gray scale lithography.

Figure 20A:
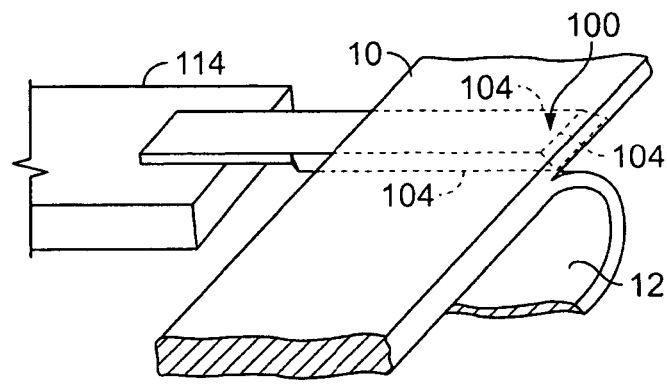
FIGS. 20A-20B shows a microknife separating a thin layer of tissue.
Figure 20B:
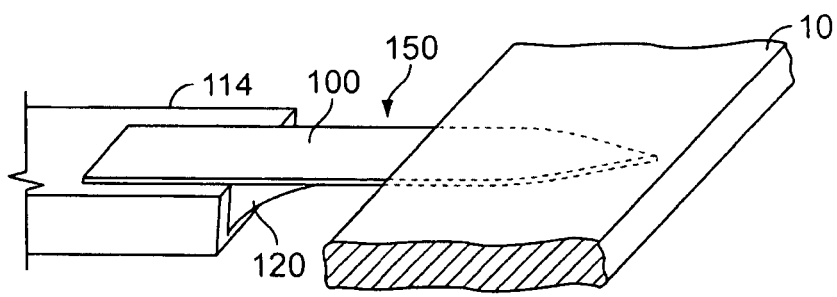

FIGS. 20A-20D show various knife-handle assemblies 150. Long knives mounted as in FIGS. 20A and 20B are useful for cutting parallel to layers of cells (such as membranes).

FIG. 20A shows a long knife blade 100 with cutting edges 104 having a square shape. As shown, due to its atomic scale, the knife blade 100 is able to separate a first layer of tissue 10 from an adjacent second layer of tissue 12 (where the second layer of tissue may be a supporting layer or the same type of tissue). FIG. 20B illustrates another knife-handle assembly 150 having a knife blade 100 with a pointed cutting end, and a fillet 120 at its base region.

FIGS. 21A-24D show knives mounted on, or embedded in, blocks 152 that physically stop the blade from cutting deeper than a predetermined depth. In one variation, the blocks 152 are transparent to allow visualization of the cutting field.

Figure 21A:
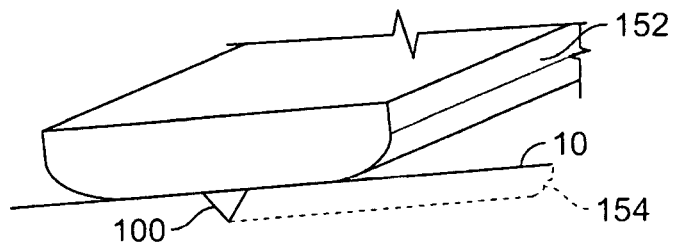
FIG. 21A shows microknives having features to limit a depth of a cut in tissue.

In some cases, the portion of the block that engages tissue is smoothed and rounded enough to slide over the tissue easily without disturbing it. The depth of cutting is limited to the length of the knife blade that extends past the surface of the block. FIG. 21A shows a side view of a knife 100 carried by a depth limiting block 152 making a cut of predetermined depth 154 in a tissue 10.

Figure 21B:
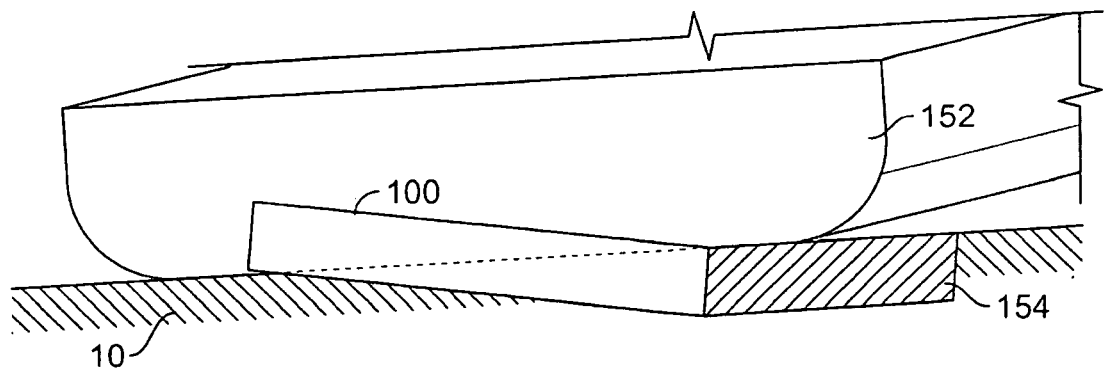
FIG. 21B shows knife with a low angle of attack making a cut of prescribed depth in tissue.

FIG. 21B shows a long knife blade 100 carried by a block 152. In this variation, the knife blade 100 is mounted at a shallow angle to minimize the force of cutting while making a cut in tissue 10 at a depth 154.

FIGS. 22A-22C show various views of a knife blade 100 embedded within a block 154. Again, the block 154 may be transparent. In this case the surgeon (or computer vision system) can clearly visualize the knife blade 100 and the tissue being cut. This visual feedback allows for appropriate force and displacement control and correction at all times during a cut. The transparent material may be glass or plastic. In one embodiment, the microknife is held in position by a mold as plastic is cast, or injection molded, around it. The knife can be moved into the tissue until block 154 comes into contact with the tissue to prevent further penetration by the knife 100. Then the knife 100 is translated across the tissue to make a cut of constant depth. The entire handle and block may be molded as one piece, or they may be molded separately and then bonded (e.g., by gluing) together.

FIGS. 23A-23D illustrate additional variations of devices. FIG. 23A shows a side view of a knife embedded in transparent plastic. In this case, the block 154 serves as a handle as well.

FIGS. 23B-23D show various views of a variation where a knife blade 100 is affixed to a block 154 rather than embedded within the block 154.

I claim:

1. A self-sharpening micro-machined knife comprising;
   a planar cutting layer having a thickness of less than 500 angstroms, the cutting layer having a first wear rate;
   a supporting layer on at least one side of the cutting layer, the supporting layer having a second wear rate and mechanically supporting the planar cutting layer, a blade edge formed by a portion of the cuffing layer and a portion of the supporting layer, where the first wear rate is less than the second wear rate such that the supporting layer wears at a faster rate than the cutting layer such that the supporting layer wears away to expose the blade edge.

2. The self-sharpening micro-machined knife of claim 1, where the supporting layer only covers one side of the cutting layer.

3. The self-sharpening micro-machined knife of claim 2, where at least a second side of the cuffing layer is exposed.

4. The self-sharpening micro-machined knife of claim 1, where the cutting layer has a greater hardness than a hardness of the supporting layer, 5. The self-sharpening micro-machined knife of claim 1, wherein the thickness of the cutting layer is no greater than 100 angstroms.

6. The self-sharpening micro-machined knife of claim 1, wherein the thickness of the cutting layer is no greater than 50 angstroms.

7. The self-sharpening micro-machined knife of claim 1, wherein the thickness of the cutting layer is no greater than 25 angstroms.

8. The self-sharpening micro-machined knife of claim 1. where the cutting layer comprises two sub-layers joined together, where each sublayer includes a crystal plane and each crystal plane of the respective sublayer is aligned so that the crystal planes meet at a single line.

9. The self-sharpening micro-machined knife of claim 1, where the second wear rate of the supporting layer increases in a direction away from the cutting layer.

10. The self-sharpening micro-machined knife of claim 9, where the second wear rate of the supporting layer increases in porosity in the direction away from the cutting layer.

11. The self-sharpening micro-machined knife of claim 10, further including a biologically active component in the supporting layer.

12. The self-sharpening micro-machined knife of claim 11, where the biologically active component is located in pores of the supporting layer.

13. The self-sharpening micro-machined knife of claim 11, where the biologically active component comprises a component selected from the group consisting of a medicine, a pharmacologically active chemical compound, a chemical compound, a protein a combination of proteins, RNA, and DNA, 14. The self-sharpening micro-machined knife of claim 10, further including a lubricant in the supporting layer.

15. The self-sharpening micro-machined knife of claim 9, where the supporting layer comprises a silicon nitride material and where a percentage of silicon in the silicon nitride increases in the direction away from the cutting layer.

16. The self-sharpening micro-machined knife of claim 15, where the percentage of silicon increases and the percentage of nitrogen decreases such that an exterior surface of the supporting layer is substantially all silicon.

17. The self-sharpening micro-machined knife of claim 9, where the supporting layer comprises a silicon carbide material and where percentage of silicon in the silicon carbide increases in the direction away from the cutting layer.

18. The self-sharpening micro-machined knife of claim 17, where the percentage of silicon increases and the percentage of carbon decreases such that an exterior surface of the supporting layer is substantially all silicon.

19. The self-sharpening micro-machined knife of claim 9, where the second wear rate of the supporting layer increases over the thickness of the supporting layer with increasing distance from the cutting layer.

20. The self-sharpening micro-machined knife of claim 9, where the cutting layer is located on a substrate.

21. The self-sharpening micro-machined knife of claim 20, further comprising a. reservoir in the substrate.

22. The self-sharpening micro-machined knife of claim 21, further comprising at least one fluidic channel in fluid communication between the reservoir and a surface of the supporting layer, 23. The self-sharpening micro-machined knife of claim 22, further comprising a lubricant and/or biologically active component in the reservoir.

24. The self-sharpening micro-machined knife of claim 1, where the supporting layer and/or cutting layer is attached to a handle.

25. The self-sharpening micro-machined knife of claim 24, further comprising a flexure coupled to the handle.

26. The self-sharpening micro-machined knife of claim 24, further comprising an actuator coupled to the handle.

27. The self-sharpening micro-machined knife of claim 24, further comprising, an electrode coupled to the handle and/or supporting, layer.

28. The self-sharpening micro-machined knife of claim 1, where the supporting layer and cutting layer form a curved blade shape.

29. The self-sharpening micro-machined knife of claim 1, further comprising a catheter body coupled to the supporting layer, 30. The self-sharpening micro-machined knife of claim 29, where the catheter body comprises a microcatheter having a diameter no greater than 2 mm.

31. The self-sharpening micro-machined knife of claim 1, further having a handle coupled to the supporting layer.

32. The self-sharpening micro-machined knife of claim 31, where the handle comprises a transparent material.

33. The self-sharpening micro-machined knife of claim 31, where the handle comprises a surface, where the cutting. layer and supporting layer extend from the surface such that the surface limits a depth of penetration of the cutting layer.

* * * * *